United States Patent [19]

Jamison et al.

[11] Patent Number: 5,652,213
[45] Date of Patent: Jul. 29, 1997

[54] CYCLIC PEPTIDE ANTIFUNGAL AGENTS

[75] Inventors: James A. Jamison; Michael J. Rodriguez, both of Indianapolis, Ind.; Lisa M. H. LaGrandeur, Tucson, Ariz.; William W. Turner, Bloomington; Mark J. Zweifel, Indianapolis, both of Ind.

[73] Assignee: Eli Lilly and Company, Indianapolis, Ind.

[21] Appl. No.: 613,949

[22] Filed: Mar. 11, 1996

Related U.S. Application Data

[63] Continuation of Ser. No. 453,052, May 26, 1995.

[51] Int. Cl.$^6$ .......................... C07K 14/755; C07K 7/56; C07K 7/64
[52] U.S. Cl. ..................... 514/11; 514/9; 530/317
[58] Field of Search ..................... 530/317; 514/9, 514/11

[56] References Cited

U.S. PATENT DOCUMENTS

| | | |
|---|---|---|
| 4,293,488 | 10/1981 | Debono . |
| 4,293,489 | 10/1981 | Debono . |
| 4,320,052 | 3/1982 | Abbott et al. . |
| 5,166,135 | 11/1992 | Schmatz . |

FOREIGN PATENT DOCUMENTS

| | | |
|---|---|---|
| 359529 | 3/1990 | European Pat. Off. . |
| 448355 | 9/1991 | European Pat. Off. . |
| 447186 | 9/1991 | European Pat. Off. . |
| 448343 | 9/1991 | European Pat. Off. . |
| 448356 | 9/1991 | European Pat. Off. . |
| 448353 | 9/1991 | European Pat. Off. . |
| 448354 | 9/1991 | European Pat. Off. . |
| 462531 | 12/1991 | European Pat. Off. . |
| 503960 | 9/1992 | European Pat. Off. . |
| 0 535 967 A2 | 10/1992 | European Pat. Off. . |
| 0 538 002 A1 | 10/1992 | European Pat. Off. . |
| 525889 | 2/1993 | European Pat. Off. . |
| 561639 | 9/1993 | European Pat. Off. . |
| 2241956 | 9/1991 | United Kingdom . |
| 2242194 | 9/1991 | United Kingdom . |
| WO94/25045 | 4/1994 | WIPO . |
| WO94/25048 | 4/1994 | WIPO . |
| WO94/25050 | 4/1994 | WIPO . |
| WO95/08341 | 9/1994 | WIPO . |

*Primary Examiner*—Howard E. Schain
*Attorney, Agent, or Firm*—Janet T. McClain; David E. Boone

[57] ABSTRACT

Provided are pharmaceutical formulations, and methods of inhibiting fungal and parasitic activity using a compound of formula I:

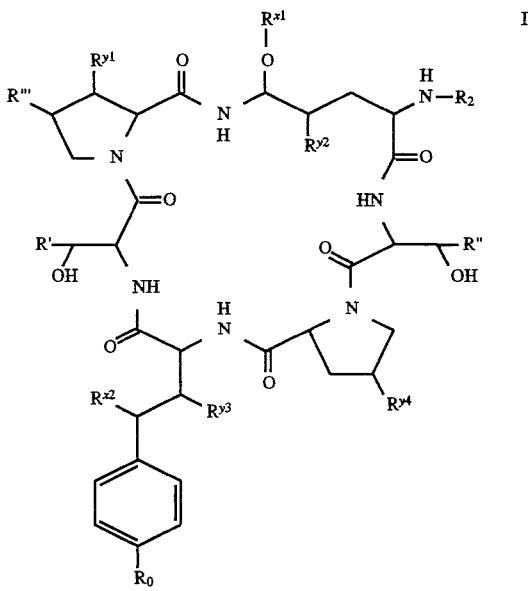

wherein R', R", $R^{x1}$, $R^{x2}$, $R^{y1}$–$R^{y4}$, $R^{z1}$, $R^{z2}$, a, b, c, d, e, $R^0$, $R^1$ and $R^2$ are defined as in the specification.

65 Claims, No Drawings

CYCLIC PEPTIDE ANTIFUNGAL AGENTS

This application is a continuation of application Ser. No. 08/453,052, filed on May 26, 1995.

BACKGROUND OF THE INVENTION

This invention relates to semi-synthetic cyclic peptide compounds which are useful as antifungal and antiparasitic agents and which have improved stability and water solubility. In particular, it relates to derivatives of the echinocandin class of cyclic peptides; to methods for treating fungal and parasitic infections, and to formulations useful in the methods.

The compounds provided by this invention are semi-synthetic compounds derived from cyclic peptides which are produced by culturing various microorganisms. A number of cyclic peptides are known in the art including echinocandin B (A30912A), aculeacin, mulundocandin, sporiofungin and S31794/F1.

In general, these cyclic peptides may be structurally characterized as a cyclic hexapeptide core (or nucleus) with an acylated amino group on one of the core amino acids. The amino group is typically acylated with a fatty acid group forming a side chain off the nucleus. For example, echinocandin B has a linoleoyl side chain while aculeacin has a palmitoyl side chain.

The fatty acid side chains may be removed from the cyclic peptide core to provide an amino nucleus (for example, a compound of formula I, below, where $R_2$ is hydrogen). The amino group may then be re-acylated to provide semi-synthetic compounds such as those claimed in the present application.

The echinocandin B nucleus has been re-acylated with certain non-naturally occurring side chain moieties to provide a number of antifungal agents (see, Debono, U.S. Pat. No. 4,293,489). Among such antifungal agents is cilofungin which is represented by a compound of formula I where $R'$, $R''$ and $R'''$ are methyl; $R^{x1}$ is hydrogen, $R^{x2}$, $R^{y1}$, $R^{y2}$, $R^{y3}$, $R^{y4}$ and $R_0$ is hydroxy and $R_2$ is p-(octyloxy)benzoyl.

SUMMARY OF THE INVENTION

The present invention provides a compound of formula I:

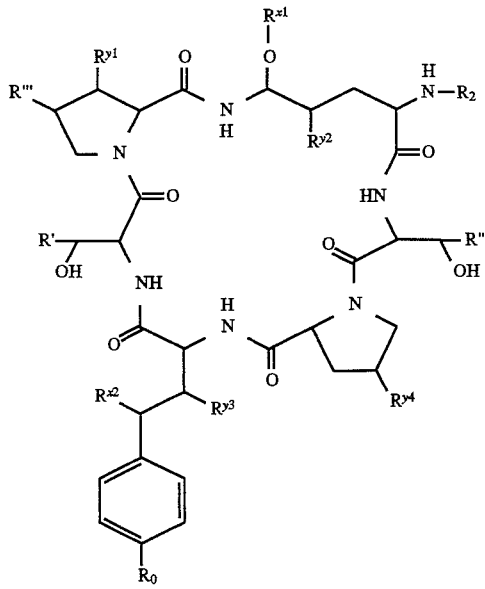

wherein:

$R'$ is hydrogen, methyl or $-CH_2C(O)NH_2$;

$R''$ and $R'''$ are independently hydrogen or methyl;

$R^{x1}$ is $C_1-C_6$ alkyl, benzyl, $-(CH_2)_2Si(CH_3)_3$, $-CH_2CH=CH_2$, $-CH_2CHOHCH_2OH$, $-(CH_2)_a$COOH, $-(CH_2)_bNR^{z1}R^{z2}$, $-(CH_2)_cPOR^{z3}R^{z4}$ or $-[(CH_2)_2O]_d-(C_1-C_6)$alkyl;

a, b and c are independently 1, 2, 3, 4, 5 or 6;

$R^{z1}$ and $R^{z2}$ are independently hydrogen, $C_1-C_6$ alkyl, or $R^{z1}$ and $R^{z2}$ combine to form $-CH_2(CH_2)_eCH_2-$;

$R^{z3}$ and $R^{z4}$ are independently hydroxy, or $C_1-C_6$ alkoxy;

d is 1 or 2;

e is 1, 2 or 3;

$R^{x2}$, $R^{y1}$, $R^{y2}$, $R^{y3}$ and $R^{y4}$ are independently hydroxy or hydrogen;

$R_0$ is hydroxy, $-OP(O)(OH)_2$ or a group of the formulae:

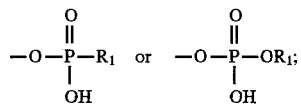

$R_1$ is $C_1-C_6$ alkyl, phenyl, p-halo-phenyl, p-nitrophenyl, benzyl, p-halo-benzyl or p-nitro-benzyl;

I) $R_2$ is a group of the formula

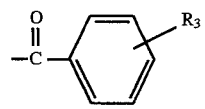

where:

A) $R_3$ is $C_1-C_{12}$ alkyl, $C_1-C_6$ alkoxy or quinolyl;

B) $R_3$ is $-O-(CH_2)_m-[O-(CH_2)_n]_p-O-(C_1-C_{12}$ alkyl);

m and n are independently 2, 3 or 4;

p is 0 or 1; or

C) $R_3$ is $-Y-(C_1-C_{12}$ alkyl);

Y is $-C\equiv C-$ or $-CH=CH-$; or

D) $R_3$ is $-O-(CH_2)_q-G$;

q is 2, 3 or 4;

G is $C_7-C_{10}$ bicycloalkyl or $C_7-C_{14}$ tricycloalkyl; or

II) $R_2$ is a group of the formula

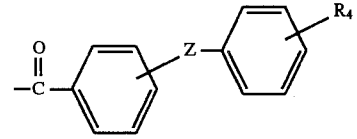

where:

Z is $-O-$, $-C\equiv C-$, $-CH=CH-$, $-CH_2-CH_2-$, $-CH_2-$, or a bond;

A) $R_4$ is hydrogen, $C_1-C_{12}$ alkyl, $C_1-C_{12}$ substituted alkyl, $C_2-C_{12}$ alkenyl, $C_2-C_{12}$ substituted alkenyl, $C_2-C_{12}$ alkynyl, $C_2-C_{12}$ substituted alkynyl, $C_1-C_{12}$ alkoxy, $C_3-C_{12}$ cycloalkyl, $C_7-C_{10}$ bicycloalkyl, $C_7-C_{14}$ tricycloalkyl, $C_3-C_{12}$ cycloalkoxy, naphthyl, pyridyl, thienyl, benzothienyl, quinolyl or phenyl; or B) $R_4$ is phenyl substituted by amino, $C_1-C_{12}$ alkylthio, halo, $C_1-C_{12}$ alkyl, $C_2-C_{12}$ alkenyl, $C_2-C_{12}$ alkynyl, $C_1-C_{12}$ substituted alkyl, $C_2-C_{12}$ substituted alkenyl, $C_2-C_{12}$ substituted alkynyl, $C_1-C_{12}$ alkoxy, trifluoromethyl, phenyl, substituted phenyl, or phenyl substituted with a group of the formula $-O-(CH_2)_m-[O-(CH_2)_n]_p-O-(C_1-C_{12}$ alkyl) where m, n and p are as defined above; or C) $R_4$ is $C_1$–$C_{12}$ alkoxy substituted with halo, $C_3$–$C_{12}$ cycloalkyl, $C_7$–$C_{10}$ bicycloalkyl, $C_7$–$C_{14}$ tricycloalkyl, $C_1$–$C_6$ alkoxy, $C_2$–$C_{12}$ alkynyl, amino, $C_1$–$C_4$ alkylamino, di($C_1$–$C_4$ alkyl)amino, formamido, $C_2$–$C_{12}$ alkanoylamino, or phenyl substituted with a group of the formula —O—$(CH_2)_m$—[O—$(CH_2)_n]_p$—O—($C_1$–$C_{12}$ alkyl) where m, n and p are as defined above; or D) $R_4$ is —O—$(CH_2)_r$—W—$R_5$;
r is 2, 3 or 4;
W is pyrrolidino, piperidino or piperazino;
$R_5$ is hydrogen, $C_1$–$C_{12}$ alkyl, $C_3$–$C_{12}$ cycloalkyl, benzyl or $C_3$–$C_{12}$ cycloalkylmethyl; or E) $R_4$ is —$Y^1$—$R_6$;
$Y^1$ is —C≡C— or —CH=CH—;
$R_6$ is $C_3$–$C_{12}$ cycloalkyl, $C_7$–$C_{10}$ bicycloalkyl, $C_7$–$C_{14}$ tricycloalkyl, $C_3$–$C_{12}$ cycloalkenyl, naphthyl, benzothiazolyl, thienyl, indanyl, fluorenyl, or phenyl substituted with $C_1$–$C_{12}$ alkylthio, $C_2$–$C_{12}$ alkenyl, $C_2$–$C_{12}$ alkynyl, halo($C_1$–$C_6$ alkoxy) or a group of the formula —O—$(CH_2)_r$—W—$R_5$ where r, W and $R_5$ are as defined above; or
$R_6$ is phenyl substituted with a group of the formula —O—$(CH_2)_m$—[O—$(CH_2)_n]_p$—O—($C_1$–$C_{12}$ alkyl) where m, n and p are as defined above; or F) $R_4$ is $C_1$–$C_{12}$ alkoxy substituted with a group of the formula —NHC(O)$R_7$;
$R_7$ is $C_1$–$C_6$ alkoxy, or phenyl($C_1$–$C_6$ alkoxy); or III) $R_2$ is a group of the formula

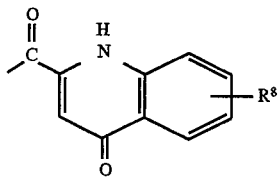

where $R^8$ is $C_1$–$C_{12}$ alkoxy or a group of the formula —O—$(CH_2)_m$—[O—$(CH_2)_n]_p$—O—($C_1$–$C_{12}$ alkyl) where m, n and p are as defined above; or IV) $R_2$ is a group of the formula

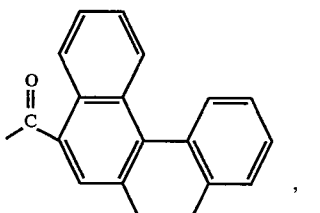

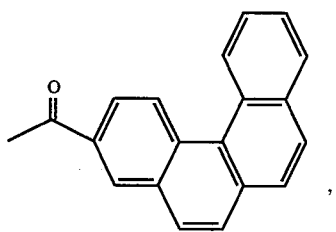

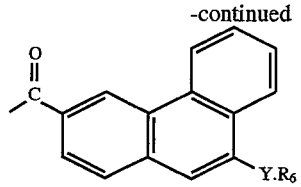

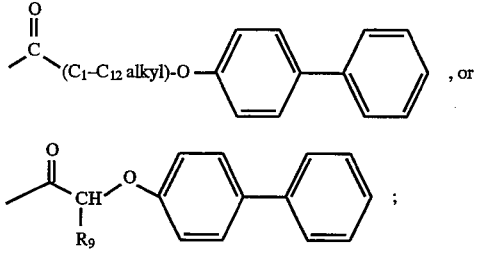

where:
Y and $R_6$ are as defined above;
$R_9$ is phenyl, $C_1$–$C_{12}$ alkyl, or $C_1$–$C_{12}$ alkoxy; or V) $R_2$ is naphthoyl substituted with $R_4$ where $R_4$ is as defined above;
with the provisos that
i) when R' is —$CH_2C(O)NH_2$; and $R^{x1}$ is methyl or benzyl; then $R_2$ is not a group of the formula

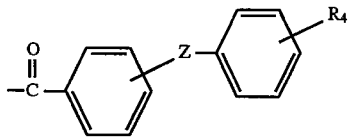

where:
Z is a bond;
A) $R_4$ is $C_1$–$C_{12}$ alkoxy; or
B) $R_4$ is phenyl substituted by $C_1$–$C_{12}$ alkoxy; or
C) $R_4$ is $C_1$–$C_{12}$ alkoxy substituted with $C_1$–$C_4$ alkylamino, di($C_1$–$C_4$ alkyl)amino; or
D) $R_4$ is —O—$(CH_2)_r$—W—$R_5$;
W is piperidino or piperazino;

ii) when $R^{x1}$ is —$(CH_2)_b NR^{z1}R^{z2}$; then $R_2$ is not a group of the formula

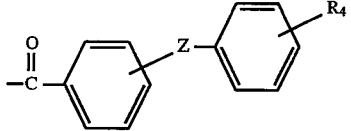

where:
Z is a bond;
A) $R_4$ is $C_1$–$C_{12}$ alkoxy; or
B) $R_4$ is phenyl substituted by $C_1$–$C_{12}$ alkoxy; or
C) $R_4$ is $C_1$–$C_{12}$ alkoxy substituted with $C_1$–$C_4$ alkylamino, di($C_1$–$C_4$ alkyl)amino; or
D) $R_4$ is —O—$(CH_2)_r$—W—$R_5$;
W is piperidino or piperazino;
or a pharmaceutically acceptable salt thereof.

Also provided are pharmaceutical formulations, methods for inhibiting parasitic or fungal activity and methods of treating fungal or parasitic infections which employ the compounds of the invention.

DETAILED DESCRIPTION

As used herein, the term "$C_1$–$C_{12}$ alkyl" refers to a straight or branched alkyl chain having from one to twelve carbon atoms. Typical $C_1-C_{12}$ alkyl groups include methyl, ethyl, propyl, isopropyl, butyl, sec-butyl, t-butyl, pentyl, 5-methylpentyl, hexyl, heptyl, 3,3-dimethylheptyl, octyl, 2-methyl-octyl, nonyl, decyl, undecyl, dodecyl and the like. The term "$C_1-C_{12}$ alkyl" includes within its definition the terms "$C_1-C_6$ alkyl" and "$C_1-C_4$ alkyl."

The term "halo" refers to chloro, fluoro, bromo or iodo.

The term "$C_2-C_{12}$ alkenyl" refers to a straight or branched alkenyl chain having from two to twelve carbon atoms. Typical $C_2-C_{12}$ alkenyl groups include ethenyl, 1-propen-2-yl, 3-buten-1-yl, 1-buten-2-yl, 1-buten-1-yl, 1-penten-3-yl, 2-hexen-3-yl, 1-decen-2-yl, 2-decen-5-yl and the like.

The term "$C_2-C_{12}$ alkynyl" refers to a straight or branched alkynyl chain having from two to twelve carbon atoms. Typical $C_2-C_{12}$ alkynyl groups include ethynyl, 1-propyn-1-yl, 1-propyn-2-yl, 1-butyn-1-yl, 1-butyn-3-yl, 1-pentyn-3-yl, 4-pentyn-2-yl, 1-hexyn-3-yl, 3-hexyn-1-yl, 5-methyl-3-hexyn-1-yl, 5-octyn-1-yl, 7-octyn-1-yl, 4-decyn-1-yl, 6-decyn-1-yl and the like.

The term "$C_1-C_{12}$ alkylthio" refers to a straight or branched alkyl chain having from one to twelve carbon atoms attached to a sulfur atom. Typical $C_1-C_{12}$ alkylthio groups include methylthio, ethylthio, propylthio, isopropylthio, butylthio, 3-methyl-heptylthio, octylthio, 5,5-dimethylhexylthio and the like.

The term "$C_1-C_{12}$ alkoxy" refers to a straight or branched alkyl chain having from one to twelve carbon atoms attached to an oxygen atom. Typical $C_1-C_{12}$ alkoxy groups include methoxy, ethoxy, propoxy, butoxy, sec-butoxy, pentoxy, 5-methyl-hexoxy, heptoxy, octyloxy, decyloxy dodecyloxy and the like. The term "$C_1-C_{12}$ alkyl" includes within its definition the terms "$C_1-C_6$ alkoxy" and "$C_1-C_4$ alkoxy."

The terms "$C_1-C_{12}$ substituted alkyl," "$C_2-C_{12}$ substituted alkenyl" and "$C_2-C_{12}$ substituted alkynyl," refers to the specified moiety substituted with 1 or 2 substituents independently selected from halo, hydroxy, protected hydroxy, amino, protected amino, $C_1-C_7$ acyloxy, nitro, carboxy, protected carboxy, carbamoyl, carbamoyloxy, cyano, methylsulfonylamino, phenyl, substituted phenyl or $C_1-C_{12}$ alkoxy.

The term "substituted phenyl" refers to a phenyl group substituted with 1, 2 or 3 substituents independently selected from halo, hydroxy, protected hydroxy, cyano, nitro, $C_1-C_{12}$ alkyl, $C_1-C_{12}$ alkoxy, carboxy, protected carboxy, carboxymethyl, hydroxymethyl, amino, aminomethyl trifluoromethyl or N-methylsulfonylamino.

The term "$C_3-C_{12}$ cycloalkyl" refers a saturated hydrocarbon ring structure having from three to twelve carbon atoms. Typical $C_3-C_{12}$ cycloalkyl groups include cyclopropyl, cyclobutyl, cyclopentyl, cyclohexyl and cycloheptyl, cyclooctyl and the like.

The term "$C_3-C_{12}$ cycloalkoxy" refers to a $C_3-C_{12}$ cycloalkyl group attached to an oxygen atom. Typical $C_3-C_{12}$ cycloalkoxy groups include cyclopropyloxy, cyclobutyloxy, cyclopentyloxy, cyclohexyloxy and cycloheptyloxy and the like.

The term "$C_3-C_{12}$ cycloalkenyl" refers to a hydrocarbon ring structure having from three to twelve carbon atoms with at least one double bond. Typical $C_3-C_{12}$ cycloalkenyl groups include cyclopropenyl, cyclobutenyl, cyclopentenyl and the like.

The term "methyl($C_3-C_{12}$ cycloalkyl)" refers to a $C_3-C_{12}$ cycloalkyl group that is substituted with a methyl group. Typical methyl($C_3-C_{12}$ cycloalkyl) groups include 2-methylcycloproyl, 2-methylcyclobutyl, 3-methylcyclopentyl, 4-methylcyclohexyl and the like.

The term "$C_1-C_4$ alkylamino" refers to a straight or branched alkylamino chain having from one to four carbon atoms attached to a nitrogen atom. Typical $C_1-C_4$ alkylamino groups include methylamino, ethylamino, propylamino, isopropylamino, butylamino, sec-butylamino and the like.

The term "di($C_1-C_4$ alkyl)amino" refers to a di($C_1-C_4$ alkyl)amino chain having two straight or branched alkyl chains of from one to four carbon atoms attached to a common nitrogen atom. Typical di($C_1-C_4$ alkyl)amino groups include dimethylamino, diethylamino, ethylmethylamino, methylisopropyl-amino, dipropylamino, dibutylamino, methylbutylamino, t-butylisopropylamino, di-t-butylamino and the like.

The term "$C_2-C_{12}$ alkanoyl" represents a straight or branched chain alkyl chain having from one to four carbon atoms attached to a carbonyl moiety. Typical $C_2-C_{12}$ alkanoyl groups include ethanoyl, propanoyl, isopropanoyl, butanoyl, isobutanoyl, sec-butanoyl, t-butanoyl, pentanoyl and the like.

The term "$C_2-C_{12}$ alkanoylamino" represents a straight or branched chain alkyl group attached to a carbonylamino moiety. Typical $C_2-C_{12}$ alkanoylamino groups include ethanoylamino, propanoylamino, isopropanoylamino, butanoyl-amino, isobutanoylamino, sec-butanoylamino, t-butanoylamino, pentanoylamino and the like.

The terms "$C_7-C_{10}$ bicycloalkyl" represents two fused cycloalkyl rings having a total of seven to ten carbon atoms and "$C_7-C_{14}$ tricycloalkyl" represents three fused cycloalkyl rings having a total of seven to fourteen carbon atoms. Typical "$C_7-C_{10}$ bicycloalkyl" and "$C_7-C_{14}$ tricycloalkyl" groups include bicyclo[2.2.1.]hept-2-yl, bicyclo[2.2.1.]hept-4-en-2-yl, bicyclo[3.3.1.]non-3-yl, bicyclo[3.3.1.]non-2-yl, bicyclo[3.2.1.]oct-2-yl, bicyclo[2.2.2.]oct-2-yl, bicyclo[2.2.2]oct-5-en-2-yl, adamantyl and the like.

The term "amino-protecting group" as used in the specification refers to substituents of the amino group commonly employed to block or protect the amino functionality while reacting other functional groups on the compound. Examples of such amino-protecting groups include formyl, trityl, phthalimido, trichloroacetyl, chloroacetyl, bromoacetyl, iodoacetyl groups, or urethane-type blocking groups such as benzyloxycarbonyl, 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, t-butoxycarbonyl, 2-(4-xenyl) isopropoxycarbonyl, 1,1-diphenyleth-1-yloxycarbonyl, 1,1-diphenylprop-1-yloxycarbonyl, 2-phenylprop-2-yloxycarbonyl, 2-(p-toluyl)-prop-2-yloxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl)-ethoxycarbonyl, 2-(methylsulfonyl)ethoxycarbonyl, 2-(triphenylphosphino)-ethoxycarbonyl, fluorenylmethoxy-carbonyl ("FMOC"), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2- trichloroethoxycarbonyl, 2-ethynyl-2-propoxycarbonyl, cyclopropylmethoxycarbonyl, 4-(decyloxy) benzyloxycarbonyl, isobornyloxycarbonyl, 1-piperidyloxycarbonyl and the like; benzoylmethylsulfonyl, 2-nitrophenylsulfenyl, diphenylphosphine oxide and like amino-protecting groups. The species of amino-protecting group employed is not critical so long as the derivatized amino group is stable to the condition of subsequent reaction(s) on other positions of the intermediate molecule and can be selectively removed at the appropriate point without disrupting the remainder of the molecule including any other amino-protecting group(s). Preferred amino-protecting groups are t-butoxycarbonyl (t-Boc), allyloxycarbonyl and benzyloxycarbonyl (CbZ). Further examples of groups referred to by the above terms are described by J. W. Barton, "Protective Groups in Organic Chemistry", J. G. W. McOmie, Ed., Plenum Press, New York, N.Y., 1973, Chapter 2, and T. W. Greene, "Protective Groups in Organic Synthesis", John Wiley and sons, New York, N.Y., 1981, Chapter 7.

The term "inhibiting", i.e. a method of inhibiting parasitic or fungal activity, includes stopping, retarding or prophylactically hindering or preventing the growth or any attending characteristics and results from the existence of a parasite or fungus.

The term "contacting", i.e. contacting a compound of the invention with a parasite or fungus, includes a union or junction, or apparent touching or mutual tangency of a compound of the invention with a parasite or fungus. However, the term does not imply any further limitations to the process, such as by mechanism of inhibition, and the methods are defined to encompass the spirit of the invention, which is to inhibit parasitic and fungal activity by the action of the compounds and their inherent antiparasitic and antifungal properties, or in other words, the compounds, used in the claimed methods are the causative agent for such inhibition.

The term "pharmaceutically acceptable salt" as used herein, refers to salts of the compounds of the above formula which are substantially non-toxic to living organisms. Typical pharmaceutically acceptable salts include those salts prepared by reaction of the compounds of the present invention with a mineral or organic acid or an inorganic base. Such salts are known as acid addition and base addition salts.

Acids commonly employed to form acid addition salts are mineral acids such as hydrochloric acid, hydrobromic acid, hydroiodic acid, sulfuric acid, phosphoric acid and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, γ-hydroxybutyrate, glycollate, tartrate, methanesulfonate, propanesulfonate, naphthalene-1-sulfonate, napththalene-2-sulfonate, mandelate and the like. Preferred pharmaceutically acceptable acid addition salts are those formed with mineral acids such as hydrochloric acid and hydrobromic acid, and those formed with organic acids such as maleic acid and methanesulfonic acid.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

It should be recognized that the particular counterion forming a part of any salt of this invention is not of a critical nature, so long as the salt as a whole is pharmacologically acceptable and as long as the counterion does not contribute undesired qualities to the salt as a whole.

Typical examples of acyl groups at $R_2$ in formula I include benzoyl substituted by a polyoxa-alkyl group such as 2-methoxyethoxy (p is 0, m is 1), 2-ethoxyethoxy (p is 0, m is 2), 2-(2-ethoxyethoxy)ethoxy (m is 2, p is 1, n is 2), 3-(2-ethoxyethoxy)propoxy, 4-(2-methoxyethoxy)butoxy, and the like, or benzoyl substituted by alkynyl groups (—C≡C—($C_1$–$C_{12}$ alkyl)) such as propynyl, butynyl, hexynyl, undecynyl, and the like, or cis or trans alkenyl groups (—$CH_2$=$CH_2$—($C_1$–$C_{12}$ alkyl)) such as propenyl, butenyl, hexenyl, decenyl and the like.

Examples of acyl groups where $R_2$ is a group of the formula

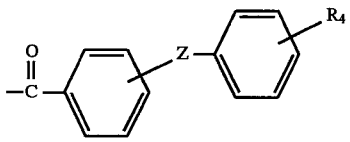

include diphenyl ethers (Z is —O—), diphenyl acetylenes (Z is —C≡C—), stilbenes (Z is —CH=CH—) and biphenyls (Z is a bond).

Examples of diphenyl ether groups include 4-(4-butoxyphenoxy)benzoyl, 4-(4-hexoxyphenoxy)benzoyl, 4-(4-ethoxyphenoxy)benzoyl, 4-(4-phenyloxyphenoxy) benzoyl, 4-[4-4-(4-dodecyloxyphenoxy)benzoyl, 4-[4-(3-dimethylaminopropoxy)phenoxy]benzoyl and the like.

Examples of diphenyl acetylene and stilbene groups include 4-styrylbenzoyl, 4-(4-methoxystyryl)benzoyl, 4-(4-butoxystyryl)benzoyl, 4-(phenylethynyl)benzoyl, 4-(4-ethoxyphenylethynyl)benzoyl, 4-(4-cyclohexyloxyphenylethynyl)benzoyl and the like.

Examples of biphenyl groups include 4-[4-(butoxy) phenyl]benzoyl, 4-[4-(cyclobutylmethoxy)phenyl]benzoyl, 4-[4-cyclopentylmethoxy)phenyl]benzoyl, 4-[4-(cyclohexylethoxy)phenyl]benzoyl, 4-[4-(hexoxy)phenyl] benzoyl, 4-phenylbenzoyl, 4-[4-(11-amino-undecyloxy) phenyl]benzoyl, 4-[4-(11-formamidoundecyloxy)phenyl] benzoyl, 4-[4-(iso-pentoxy)phenyl]benzoyl and the like.

Examples of biphenyl groups where $R_4$ is —O—$(CH_2)_r$—W—$R_5$ include 4-[4-[2-(N-cyclohexylpiperidino-4-yl) ethoxy]phenyl]benzoyl, 4-[4-[2-(N-hexylpiperidino-4-yl) ethoxy]phenyl]benzoyl, 4-[4-[2-(4-benzylpiperidino) ethoxy]phenyl]benzoyl, 4-[4-[2-(4-cyclohexylpiperidino) ethoxy]phenyl]benzoyl and the like.

Examples of biphenyl and diphenyl ether groups where $R_4$ is —$Y^1$—$R_6$ include 4-[4-(phenylethynyl)phenyl] benzoyl, 4-[4-(phenylethynyl)phenoxy]benzoyl, 4-[4-(hexynyl)phenyl]benzoyl, 4-[4-(styryl)phenoxy]benzoyl, 4-[4-[4-4-methylpiperidino)ethoxy]phenylethynyl]phenyl]benzoyl, and the like.

Acyl groups where $R_4$ is $-O-(CH_2)_r-W-R_5$ may form acid addition salts of the basic amino groups of the piperidine and piperazine heterocyclic groups with organic or mineral acids such as hydrochloric acid, hydrobromic acid, sulfuric acid and phosphoric acid and with organic acids such as the sulfonic acids, benzenesulfonic acid, toluenesulfonic acid, methanesulfonic acid, acetic acid, chloroacetic acid, trifluoroacetic acid, benzoic acid, isophthalic acid, salicylic acid, citric acid, malic acid, succinic acid, malonic acid and the like.

Table 1, below, provides further examples of acyl groups, $R_2$ found on cyclic peptides of formula I.

TABLE 1

Examples of acyl groups, $R_2$

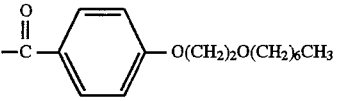
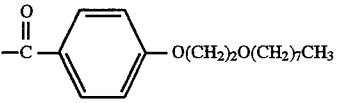
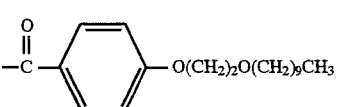
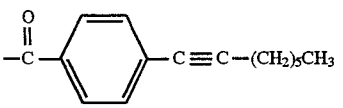
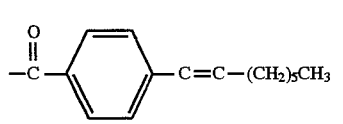
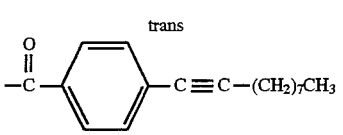
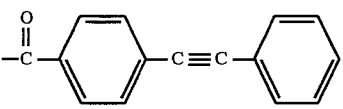
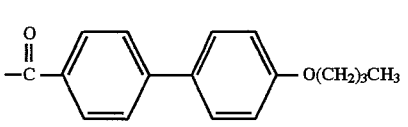
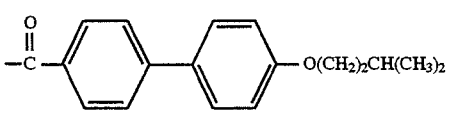
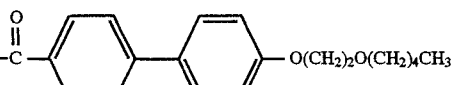
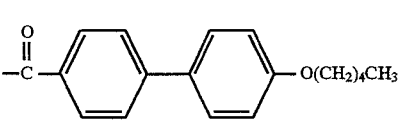

TABLE 1-continued
Examples of acyl groups, R₂
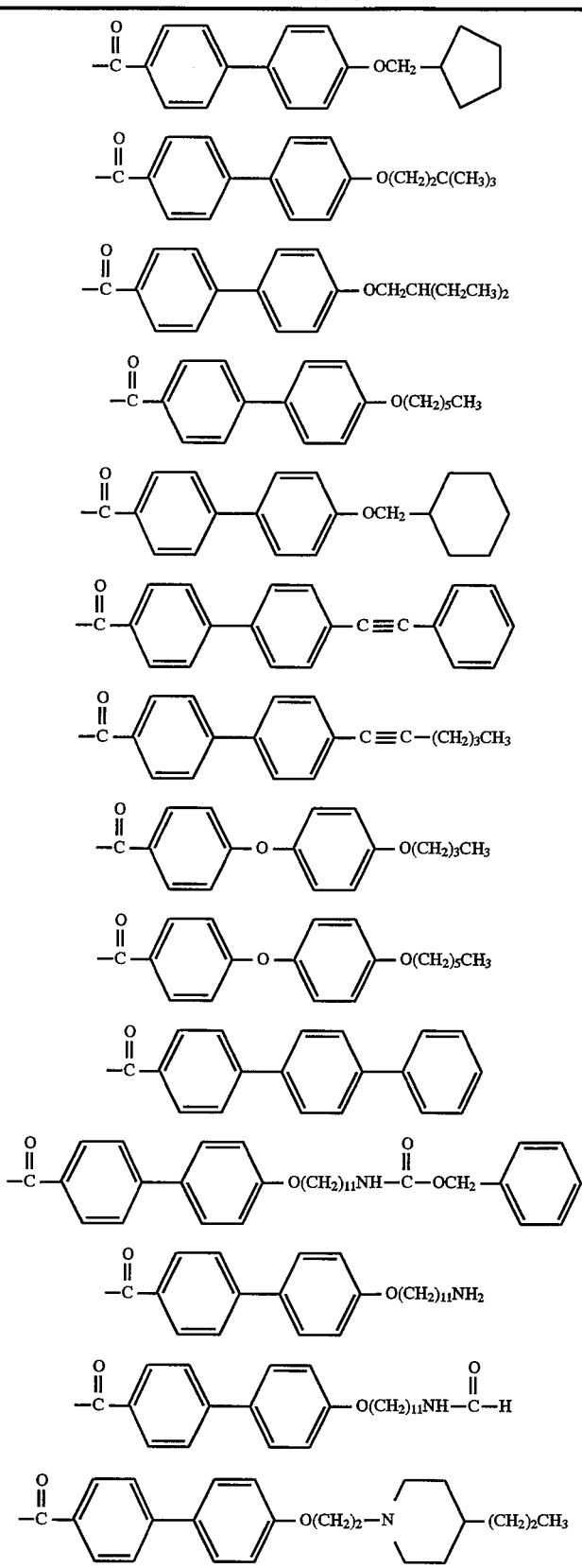

TABLE 1-continued
Examples of acyl groups, R$_2$
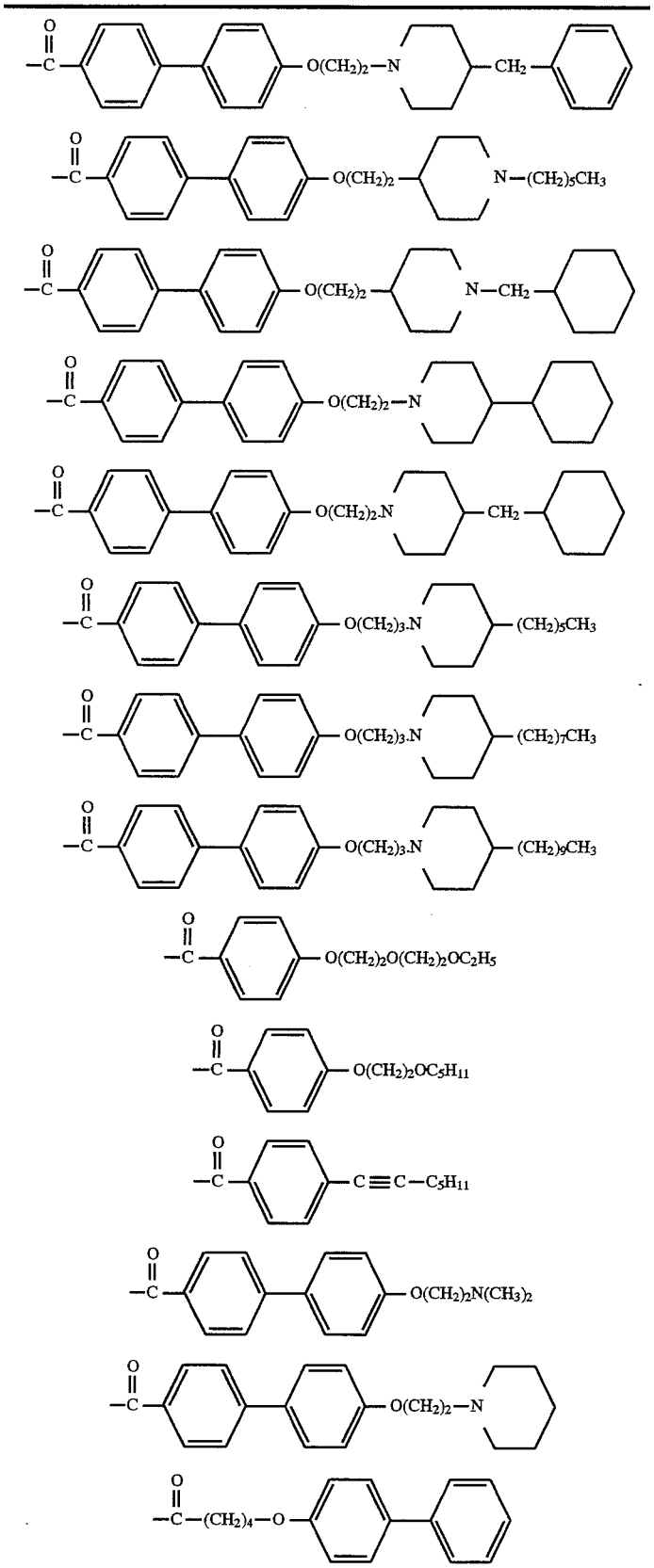

TABLE 1-continued
| Examples of acyl groups, $R_2$ |
|---|
| 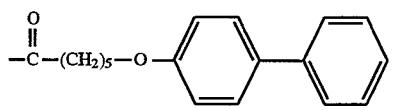 |
| 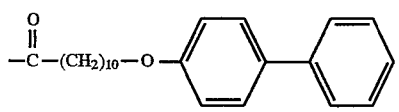 |
| 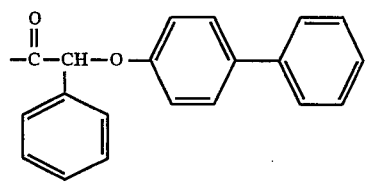 |
| 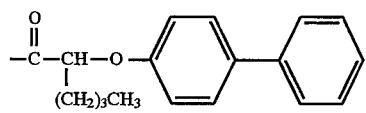 |
| 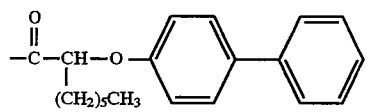 |
| 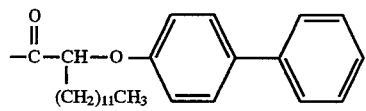 |
| 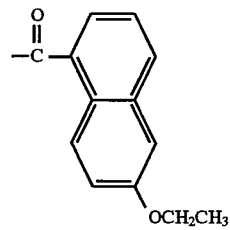 |
| 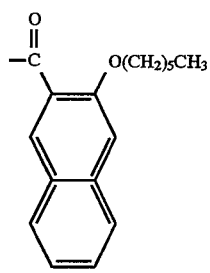 |
| 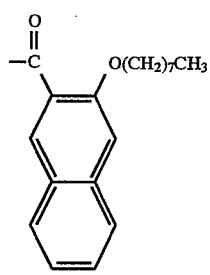 |

TABLE 1-continued
| Examples of acyl groups, R$_2$ |
|---|
| 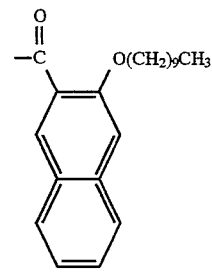 |
| 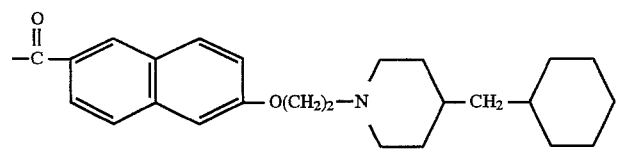 |
| 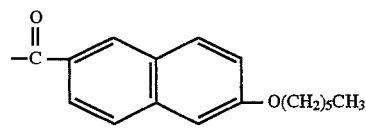 |
| 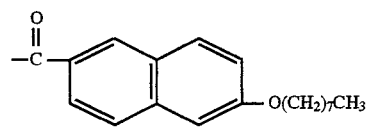 |
| 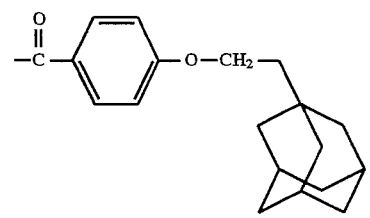 |
| 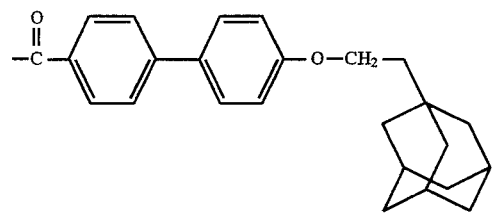 |
| 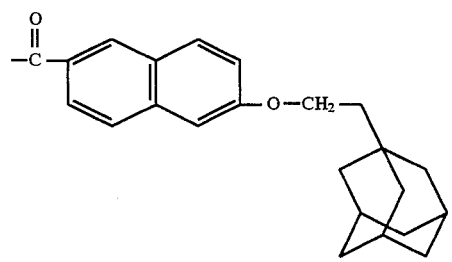 |
| 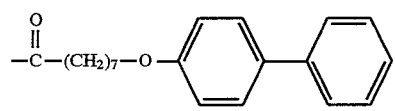 |

TABLE 1-continued

Examples of acyl groups, R$_2$

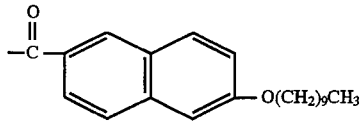

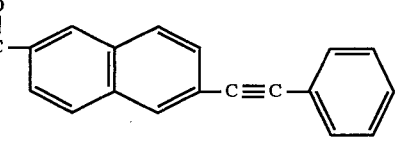

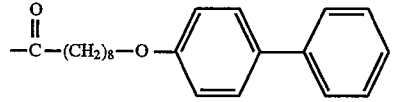

Preferred acyl groups include those groups where R$_2$ is a group of the formula:

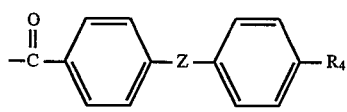

where

Z is —C≡C— or a bond;

A) R$_4$ is hydrogen, C$_1$–C$_{12}$ alkyl, C$_1$–C$_{12}$ substituted alkyl, C$_2$–C$_{12}$ alkenyl, C$_2$–C$_{12}$ substituted alkenyl, C$_2$–C$_{12}$ alkynyl, C$_2$–C$_{12}$ substituted alkynyl, C$_1$–C$_{12}$ alkoxy, C$_3$–C$_{12}$ cycloalkyl, C$_7$–C$_{10}$ bicycloalkyl, C$_7$–C$_{14}$ tricycloalkyl, C$_3$–C$_{12}$ cycloalkoxy, naphthyl, pyridyl, thienyl, benzothienyl, quinolyl or phenyl; or B) R$_4$ is phenyl substituted by amino, C$_1$–C$_{12}$ alkylthio, halo, C$_1$–C$_{12}$ alkyl, C$_2$–C$_{12}$ alkenyl, C$_2$–C$_{12}$ alkynyl, C$_1$–C$_{12}$ substituted alkyl, C$_2$–C$_{12}$ substituted alkenyl, C$_2$–C$_{12}$ substituted alkynyl, C$_1$–C$_{12}$ alkoxy, trifluoromethyl, phenyl, substituted phenyl, or a group of the formula —O—(CH$_2$)$_m$—[O—(CH$_2$)$_n$]$_p$—O—(C$_1$–C$_{12}$ alkyl) where m, n and p are as defined above; or C) R$_4$ is C$_1$–C$_{12}$ alkoxy substituted with halo, C$_3$–C$_{12}$ cycloalkyl, C$_7$–C$_{10}$ bicycloalkyl, C$_7$–C$_{14}$ tricycloalkyl, C$_1$–C$_6$ alkoxy, C$_2$–C$_{12}$ alkynyl, amino, C$_1$–C$_4$ alkylamino, di(C$_1$–C$_4$ alkyl)amino, formamido, C$_2$–C$_{12}$ alkanoylamino, or phenyl substituted with a group of the formula —O—(CH$_2$)$_m$—[O—(CH$_2$)$_n$]$_p$—O—(C$_1$–C$_{12}$ alkyl) where m, n and p are as defined above; or D) R$_4$ is —O—(CH$_2$)$_r$—W—R$_5$;
r is 2, 3 or 4;
W is pyrrolidino, piperidino or piperazino;
R$_5$ is hydrogen, C$_1$–C$_{12}$ alkyl, C$_3$–C$_{12}$ cycloalkyl, benzyl or C$_3$–C$_{12}$ cycloalkylmethyl; or E) R$_4$ is —Y$^1$—R$_6$;
Y$^1$ is —C≡C— or —CH=CH—;
R$_6$ is C$_3$–C$_{12}$ cycloalkyl, C$_7$–C$_{10}$ bicycloalkyl, C$_7$–C$_{14}$ tricycloalkyl, C$_3$–C$_{12}$ cycloalkenyl, naphthyl, benzothiazolyl, thienyl, indanyl, fluorenyl, or phenyl substituted with C$_1$–C$_{12}$ alkylthio, C$_2$–C$_{12}$ alkenyl, C$_2$–C$_{12}$ alkynyl, halo(C$_1$–C$_6$ alkoxy) or a group of the formula —O—(CH$_2$)$_r$—W—R$_5$ where r, W and R$_5$ are as defined above; or R$_6$ is phenyl substituted with a group of the formula —O—(CH$_2$)$_m$—[O—(CH$_2$)$_n$]$_p$—O—(C$_1$–C$_{12}$ alkyl) where m, n and p are as defined above; or F) R$_4$ is C$_1$–C$_{12}$ alkoxy substituted with a group of the formula —NHC(O)R$_7$;
R$_7$ is C$_1$–C$_6$ alkoxy, or phenyl(C$_1$–C$_6$ alkoxy);
or a pharmaceutically acceptable salt thereof.

Of these preferred acyl groups, more preferred are those groups where:

A) R$_4$ is C$_2$–C$_{12}$ alkynyl, C$_2$–C$_{12}$ substituted alkynyl, C$_1$–C$_{12}$ alkoxy, C$_3$–C$_{12}$ cycloalkoxy, or phenyl; or B) R$_4$ is phenyl substituted by C$_1$–C$_{12}$ alkoxy, or a group of the formula —O—(CH$_2$)$_2$—O—(C$_1$–C$_6$ alkyl); or C) R$_4$ is C$_1$–C$_{12}$ alkoxy substituted with C$_3$–C$_{12}$ cycloalkyl; or D) R$_4$ is —O—(CH$_2$)$_r$—W—R$_5$;
r is 2 or 3;
W is piperidino;
R$_5$ is hydrogen, C$_1$–C$_{12}$ alkyl, C$_3$–C$_{12}$ cycloalkyl, benzyl or C$_3$–C$_{12}$ cycloalkylmethyl; or E) R$_4$ is —Y$^1$—R$_6$;
Y$^1$ is —C≡C—;
R$_6$ is phenyl substituted with C$_1$–C$_{12}$ alkylthio, C$_2$–C$_{12}$ alkenyl, C$_2$–C$_{12}$ alkynyl, halo(C$_1$–C$_6$ alkoxy);
or R$_6$ is phenyl substituted with a group of the formula —O—(CH$_2$)$_r$—W—R$_5$ where r, W and R$_5$ are as defined above;
or R$_6$ is phenyl substituted with a group of the formula —O—(CH$_2$)$_2$—O—(C$_1$–C$_6$ alkyl);
or a pharmaceutically acceptable salt thereof.

Of these acyl groups, especially preferred are those groups where:

R$_4$ is C$_2$–C$_{12}$ alkynyl, C$_2$–C$_{12}$ substituted alkynyl, C$_1$–C$_{12}$ alkoxy, or phenyl; or R$_4$ is phenyl substituted by C$_1$–C$_{12}$ alkoxy, or a group of the formula —O—(CH$_2$)$_2$—O—(C$_1$–C$_6$ alkyl); or R₄ is —Y¹—R₆;
Y¹ is —C≡C—;
R₆ is phenyl substituted with a group of the formula
  —O—(CH₂)₂—O—(C₁-C₆ alkyl);
or a pharmaceutically acceptable salt thereof.

Of these acyl groups, the most preferred are where R₂ is one of the following groups:

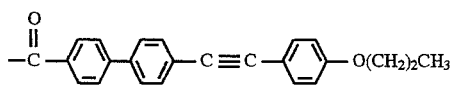

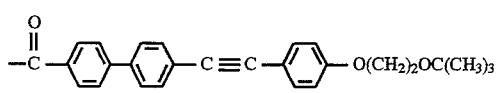

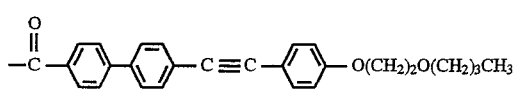

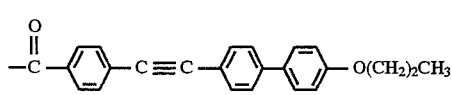

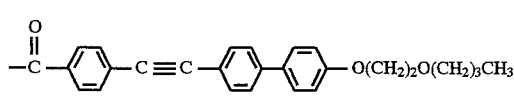

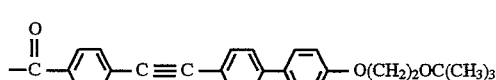

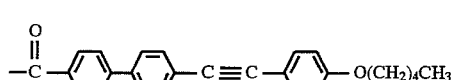

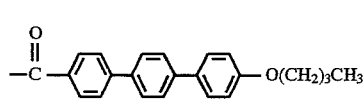

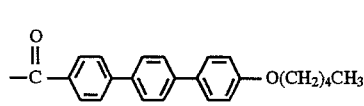

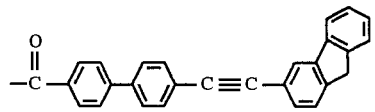

Preferred compounds of this invention are those compounds of formula I where:

R', R'', and R''' are each methyl;

$R^{y1}$, $R^{y2}$, $R^{y3}$, $R^{y4}$ are each hydroxy;

$R^{x2}$ is hydroxy;

R₀ is hydroxy or a group of the formulae:

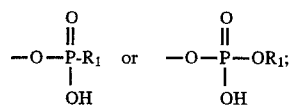

R₁ is methyl;

or a pharmaceutically acceptable salt thereof.

Of these compounds, more preferred are those compounds of formula I where:

$R^{x1}$ is C₁-C₄ alkyl, benzyl, —CH₂CHOHCH₂OH, —CH₂COOH, —(CH₂)$_b$NR$^{z1}$R$^{z2}$ or —(CH₂)₂POR$^{z3}$R$^{z4}$;

b is 2, 3, 4, 5 or 6;

R$^{z1}$ and R$^{z2}$ are independently hydrogen or C₁-C₄ alkyl; and

R$^{z3}$ and R$^{z4}$ are independently hydrogen or methoxy;

or a pharmaceutically acceptable salt thereof.

Of these compounds, further preferred are those compounds of formula I where:

$R^{x1}$ is methyl, benzyl, —CH₂CHOHCH₂OH, —CH₂COOH, —(CH₂)₂NR$^{z1}$R$^{z2}$ or —(CH₂)₂POR$^{z3}$R$^{z4}$;

R$^{z1}$ and R$^{z2}$ are independently hydrogen or methyl; and

R$^{z3}$ and R$^{z4}$ are independently hydrogen or methoxy;

or a pharmaceutically acceptable salt thereof.

Of these compounds, especially preferred are those compounds of formula I where:

$R^{x1}$ is —CH₂CHOHCH₂OH, —CH₂COOH or —(CH₂)₂POR$^{z3}$R$^{z4}$; and

R$^{z3}$ and R$^{z4}$ are independently hydrogen or methoxy;

or a pharmaceutically acceptable salt thereof.

The compounds of formula I may be prepared according to Reaction Scheme I, as follows.

Reaction Scheme I
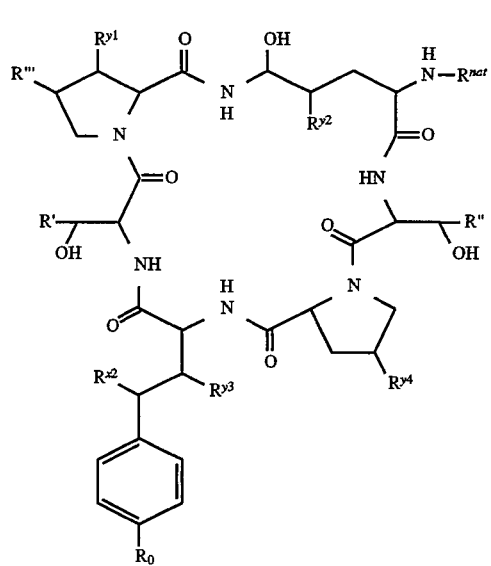
(IA)
↓ A. deacylate
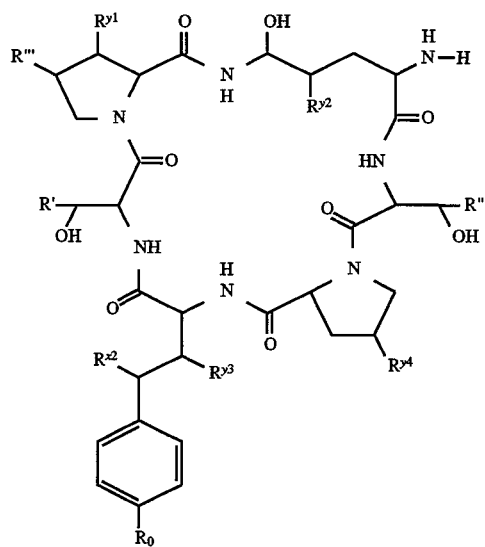
(IB)
↓ B. re-acylate
-continued
Reaction Scheme I
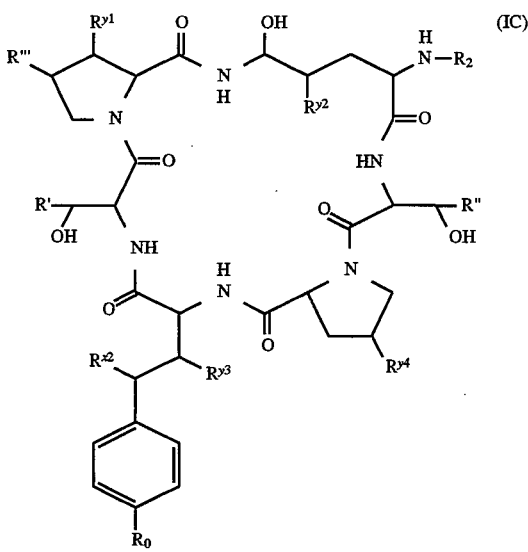
(IC)
↓ C. Etherification
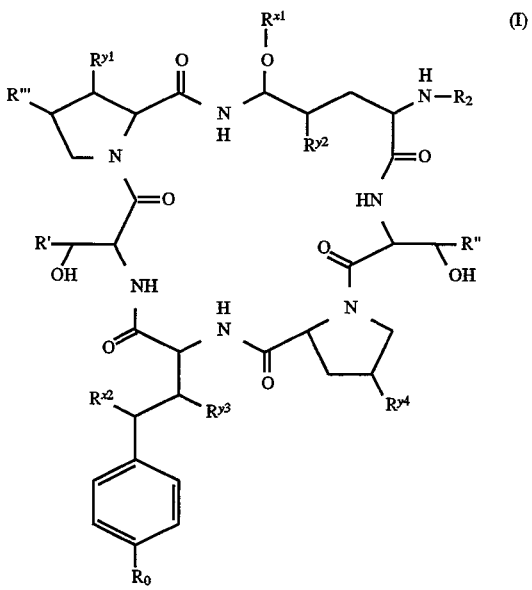
(I)
wherein:
$R^{nat}$ is a naturally occurring cyclic peptide sidechain; and R', R", R"', $R^{x1}$, $R^{x2}$, $R^{y1}$, $R^{y2}$, $R^{y3}$, $R^{y4}$, $R_0$ and $R_2$ are as defined above.

Reaction scheme I, above, is accomplished by carrying out reactions A–C, in order. Once a reaction is complete, the intermediate compound may be isolated by procedures well-known in the art, for example, the compound may be crystallized or precipitated and then collected by filtration, or the reaction solvent may be removed by extraction, evaporation or decantation. The intermediate compound may be further purified, if desired, by common techniques such as crystallization or precipitation or chromatography over solid supports such as silica gel, alumina and the like, before carrying out the next step of the reaction scheme.

In reaction IA, a naturally occurring cyclic peptide of the formula IA is deacylated using procedures known in the art to provide an amino nucleus of formula IB. This reaction is typically carried out using enzymatic deacylation by exposing the naturally occurring cyclic peptide to a deacylase enzyme. The deacylase enzyme may be obtained from the microorganism *Actinoplanes utahensis* and used substantially as described in U.S. Pat. Nos. 4,293,482 and 4,304,716, herein incorporated by reference. The deacylase enzyme may also be obtained from the Pseudomonas species. Deacylation may be accomplished using whole cells of *Actinoplanes utahensis* or Pseudomonas or the crude or purified enzyme thereof or using an immobilized form of the enzyme. See European Patent Application No. 0 460 882 (Dec. 11, 1991). Examples of naturally occurring cyclic peptides which may be used as starting materials include aculeacin (palmitoyl side chain), tetrahydroechinocandin B (stearoyl side chain), mulundocandin (branched $C_{15}$ side chain), S 31794/F1 (tetradecanoyl side chain), sporiofungin ($C_{15}$ branched side chain), FR901379 (palmitoyl side chain) and the like. A preferred naturally occurring cyclic peptide is echinocandin B (a compound of formula IA where R', R", and R'" are each methyl, $R^{x2}$, $R^{y1}$, $R^{y2}$, $R^{y3}$, $R^{y4}$ and $R_O$ are each hydroxy and $R_2$ is linoleoyl).

In Reaction IB, the resulting amino nucleus is then re-acylated using procedures known in the art to provide a compound of formula I where $R_2$ is an acyl group as defined hereinabove.

For example, the amino nucleus may be acylated by reaction with an appropriately substituted acyl halide, preferably in the presence of an acid scavenger such as a tertiary amine, such as triethylamine. The reaction is typically carried out at a temperature of from about −20° C. to about 25° C. Typical solvents for this reaction include polar aprotic solvents such as dioxane or dimethylformamide. Solvent choice is not critical so long as the solvent employed is inert to the ongoing reaction and the reactants are sufficiently solubilized to effect the desired reaction.

The amino nucleus may also be acylated by reaction with an appropriately substituted carboxylic acid, in the presence of a coupling agent. Typical coupling agents include dicyclohexylcarbodiimide (DCC), N,N'-carbonyldiimidazole, bis(2-oxo-3-oxazolidinyl)phosphinic chloride (BOP-Cl), N-ethoxycarbonyl-2-ethoxy-1,2-dihydroquinoline (EEDQ), benzotriazol-1-yloxytripyrrolidinophosphonium hexafluorophosphate (PyBOP) and the like.

In addition, the amino nucleus may be acylated with an activated ester of a carboxylic acid such as an ester of a carboxylic acid of the formula $R_2$—COOH and p-nitrophenyl, 2,4,5-trichlorophenyl, hydroxybenzotriazole hydrate (HOBT.$H_2O$), pentafluorophenol, N-hydroxysuccinimide and the like. Preferred acylating moieties are the active esters of the carboxylic acid $R_2$—COOH such as 2,4,5-trichlorophenyl ester and benzotriazole ester. The reaction is typically carried out for one to sixty five hours at a temperature from about 0° C. to about 30° C. in an aprotic solvent. The reaction is generally complete after about twenty four to forty eight hours when carried out a temperature of from about 15° C. to about 30° C. Typical solvents for this reaction are tetrahydrofuran and dimethylformamide or a mixture of such solvents. The amino nucleus is generally employed in equimolar proportions relative to the activated ester or with a slight excess of the amino nucleus.

In Reaction IC, a compound of formula IC is reacted with an appropriately substituted alcohol in the presence of an acid to provide a compound of formula I where $R^{x1}$ is $C_1$–$C_6$ alkyl, benzyl, —(CH$_2$)$_2$Si(CH$_3$)$_3$, —CH$_2$CH=CH$_2$, —(CH$_2$)$_a$COOH, —(CH$_2$)$_b$NR$^{z1}$R$^{z2}$, —(CH$_2$)$_c$POR$^{z3}$R$^{z4}$ or —[(CH$_2$)$_2$O]$_d$—(C$_1$–C$_6$)alkyl. The reaction is typically carried out in a polar aprotic solvent such as dioxane, or dimethylsulfoxide at a temperature of from about 0° C. to about 35° C., preferably at about room temperature. Solvent choice is not critical so long as the solvent employed is inert to the ongoing reaction and the reactants are sufficiently solubilized to effect the desired reaction. Preferred acids include p-toluenesulfonic acid, hydrochloric acid and camphorsulfonic acid.

The compounds of formula I where $R^{x1}$ is —(CH$_2$)$_b$NR$^{z1}$R$^{z2}$ where $R^{z1}$ and $R^{z2}$ are hydrogen may be prepared via a protected compound wherein $R^{x1}$ is —(CH$_2$)$_b$NHR$^a$ where $R^a$ is an amino protecting group. The resultant protected compound may be deprotected according to procedures known in the art.

The compounds of formula I where $R^{x1}$ is —CH$_2$CHOHCH$_2$OH may be prepared by hydroxylating a compound of formula I where $R^{x1}$ is —CH$_2$CH=CH$_2$ with osmium tetroxide in the presence of a catalyst at a temperature in the range of from about 0° C. to about 40° C. for about one to twenty four hours in a organic/aqueous solvent mixture, for example dioxane/water. Suitable catalysts include N-methylmorpholine N-oxide (NMO) and the like. Typical solvents suitable for use in this reaction include dimethylformamide, tetrahydrofuran, acetone, and dioxane. Solvent choice is not critical so long as the solvent employed is inert to the ongoing reaction and the reactants are sufficiently solubilized to effect the desired reaction. The reaction is preferably conducted at a temperature in the range of from about 20° C. to about 30° C. for about eighteen to twenty four hours.

The compounds of formula I wherein $R_O$ is hydroxy may be phosphorylated by reaction with an appropriately substituted alkyl or phenyl phosphate to provide a compound of formula I where $R_O$ is —OP(O)OH—$R_1$ where $R_1$ is $C_1$–$C_6$ alkoxy or phenoxy, or by reaction with an appropriately substituted alkyl or phenyl phosphonic acid to provide a compound of formula I where $R_O$ is —OP(O)OH—$R_1$ where $R_1$ is $C_1$–$C_6$ alkyl, or an appropriately substituted phenyl or benzyl moiety. The phosphonic acid is typically used in an activated form, for example as a phosphonic halide, preferably a phosphonic chloride. The reaction is carried out in the presence of a base such as lithium trimethylsilanolate (LiOTMS), lithium bis(trimethylsilyl)amide (LHMDS), pyridine and the like. The reaction is typically carried out for up to one hour at a temperature from about −30° C. to about 40° C. in an aprotic solvent such as tetrahydrofuran and dimethylformamide. The reaction is generally complete in about fifteen minutes when carried out under these conditions. The phosphate or phosphonate reactant is generally employed in equimolar proportions to about a one mole excess relative to the amino nucleus in the presence of an equimolar or slight excess of the base.

The cyclic peptides used to make the compounds of the present invention may be prepared by fermentation of known microorganisms. For example, the cyclic peptide of formula IB where R', R" and R'" are methyl, $R^{x2}$ is hydroxy and $R^{y1}$, $R^{y2}$, $R^{y3}$, $R^{y4}$ and $R_0$ are each hydroxy (cyclic nucleus corresponding to A-30912A) may be prepared using the procedure detailed in Abbott et al., U.S. Pat. No. 4,293, 482, which is herein incorporated by reference. The cyclic peptide of formula IB where R', R" and R'" are methyl, $R^{x2}$ is hydrogen and $R^{y1}$, $R^{y2}$, $R^{y3}$ $R^{y4}$ and $R_0$ are each hydroxy (cyclic nucleus corresponding to A-30912B) may be prepared using the procedure detailed in Abbott et al., U.S. Pat. No. 4,299,763, which is herein incorporated by reference. Aculeacin may be prepared using the procedure detailed in Mizuno et al., U.S. Pat. No. 3,978,210 which is herein incorporated by reference. The cyclic peptide of formula IB where R' is $-CH_2C(O)NH_2$, R" is methyl, R'" is hydrogen and $R^{x1}$, $R^{x2}$, $R^{y1}$, $R^{y2}$, $R^{y3}$, $R^{y4}$ and $R_0$ is hydroxy may be prepared by deacylating the cyclic peptide prepared using the procedure detailed in Chen et al., U.S. Pat. No. 5,198, 421, which is herein incorporated by reference.

The $R_2$—COOH precursor acids are prepared by hydrolyzing a nitrile of the formula $R_2$—CN or an ester of the formula $R_2$—COO($C_1$-$C_4$ alkyl). The nitrile and ester intermediates may be prepared using procedures known in the art.

For example, the nitrile and ester intermediates where $R_2$ is an alkoxy aryl moiety may be prepared using Procedure A or Procedure B, described below.

Procedure A

One equivalent of an alkyl bromide, iodide, or p-toluenesulfonate is added to a mixture containing one equivalent of a base, such as potassium t-butoxide or potassium carbonate, and one equivalent of an hydroxy aryl compound in 200–300 ml of acetonitrile. The resulting reaction mixture is refluxed for approximately six hours and then concentrated in vacuo to provide a residue. This residue is dissolved in a mixture of diethyl ether and a 2N sodium hydroxide solution. The resulting layers are separated and the organic layer is dried over magnesium sulfate, filtered and dried to provide the desired alkoxy aryl product.

Procedure B

One equivalent of diethylazodicarboxylate is added dropwise over ten minutes, at room temperature, to a mixture containing one equivalent of an hydroxy aryl compound, one equivalent of an alkyl alcohol and one equivalent of triphenylphosphine in 200–300 ml of tetrahydrofuran. After approximately seventeen hours, the solvent is removed in vacuo to provide a residue. This residue is dissolved in diethyl ether and the resulting mixture is washed with a 2N sodium hydroxide solution, dried over magnesium sulfate, filtered and concentrated to provide a product which is then crystallized from a diethyl ether/pentane mixture or, if the product contains a tertiary amine, the hydrochloride salt is formed and crystallized from a methanol/ethyl acetate mixture.

The nitrile and ester intermediates where $R_2$ is an alkynyl or alkenyl aryl moiety may be prepared using Procedure C, below.

Procedure C

A mixture containing two equivalents of triethylamine, 0.05 equivalent of palladium dichloride, 0.1 equivalent of triphenylphosphine, 0.025 equivalent of cuprous iodide and one equivalent of an alkyne or two equivalents of an alkene, is added to one equivalent of an aryl bromide, iodide, or trifluoromethanesulfonate in acetonitrile (600 ml/0.1 mol of aryl reactant), under nitrogen. The resulting mixture is refluxed for approximately seventeen hours and then the solvent is removed in vacuo to provide a residue. This residue is slurried in 300 ml of diethyl ether and then filtered to remove the resultant solids. The filtrate is washed with a 1N hydrochloric acid solution, dried over magnesium sulfate, filtered and then dried to provide the desired product.

The ester intermediates where $R_2$ is a terphenyl moiety may be prepared using Procedure D, below.

Procedure D

1. Formation of Boronic Acid Reactant

Butyl lithium (1.2 equivalents) is added to one equivalent of a cold (−78° C.) aryl halide in tetrahydrofuran. After approximately fifteen minutes, two equivalents of triisopropyl borate are added. After approximately ten minutes, the reaction mixture is warmed to room temperature, and then quenched by the addition of water, followed by the addition of a 1N hydrochloric acid solution. The resulting layers are separated and the organic layer is concentrated in vacuo to provide a solid. This solid is collected by filtration and then washed with hexane to provide a pure boronic acid product.

2. Formation of Terphenyl Ester

Tetrakis(triphenylphosphine)palladium (0.03 equivalent) is added to a mixture containing one equivalent of an aryl boronic acid, 1.5 equivalents of potassium carbonate and one equivalent of methyl 4-iodobenzoate (or trichlorophenyl ester of iodobenzoate) in nitrogen-purged toluene. The resulting reaction mixture is refluxed for approximately seven hours and then decanted to remove the potassium carbonate and dried in vacuo to provide a residue. This residue is triturated in acetonitrile and then filtered to provide the desired solid product.

The aryl nitriles and esters described above may be converted to the corresponding carboxylic acids by hydrolysis using Procedure E or Procedure F, below.

Procedure E

An aryl nitrile is dissolved in ethanol and an excess of 50% sodium hydroxide solution and refluxed for approximately two hours. Water is added to the resulting reaction mixture until a solid precipitates. This solid is collected by filtration, added to a dioxane/6N hydrochloric acid mixture and the resulting mixture is refluxed for approximately seventeen hours. When the reaction is substantially complete, the carboxylic acid product is crystallized by the addition of water and then collected by filtration and dried in vacuo.

Procedure F

An excess of a 2N sodium hydroxide solution is added to an aryl ester in methanol, and the resulting solution is refluxed for approximately five hours and then acidified by the addition of excess hydrochloric acid. Water is added to the resulting reaction mixture until a solid (carboxylic acid) precipitates. The carboxylic acid is collected by filtration and dried in vacuo.

The carboxylic acids may be converted to the corresponding 2,4,5-trichlorophenyl esters using Procedure G, below. These activated esters are then used to acylate the amino nucleus, as described above in Reaction Scheme IC.

Procedure G

A mixture containing one equivalent of an aryl carboxylic acid, one equivalent of 2,4,5-trichlorophenol, and one equivalent of N,N'-dicyclohexylcarbodiimide (DCC) in methylene chloride is stirred for approximately seventeen hours and then filtered. The filtrate is concentrated to provide a residue. This residue is dissolved in diethyl ether, filtered, and pentane is added until crystallization begins. The crystalline product is collected by filtration and dried in vacuo.

The following Preparations and Examples further describe how to synthesize the compounds of the present invention. The terms melting point, proton nuclear magnetic resonance spectra, mass spectra, infrared spectra, ultraviolet spectra, elemental analysis, high performance liquid chromatography, and thin layer chromatography are abbreviated "m.p.", "NMR", "MS", "IR", "UV", "Analysis", "HPLC", and "TLC", respectively. In addition, the absorption maxima listed for the IR spectra are only those of interest and not all of the maxima observed.

PREPARATION 1

The following nitrile and ester intermediates where $R_2$ is an alkoxy aryl moiety were prepared substantially in accordance with Procedure A, detailed above.

TABLE A

| Alkyl halide or tosylate | mass (g) | Alkoxy aryl product | mass (g) |
|---|---|---|---|
| I—(CH₂)₃CH₃ | 9.4 |  | 3.2 |
|  | 12.3 |  | 5.3 |
| Br—(CH₂)₂CH(CH₃)₂ | 7.7 |  | 9.2 |
|  | 7.6 |  | 4.8 |
| Br—(CH₂)₄CH₃ | 15.3 |  | 20.3 |
|  | 13.0 |  | 12.2 |
|  | 13.1 |  | 11.8 |
| Br—CH₂CH(CH₂CH₃)₂ | 8.5 |  | 3.0 |
| I—(CH₂)₅CH₃ | 10.8 |  | 11.4 |
|  | 4.2 |  | 4.5 |
|  | 23.4 |  | 20.9 |
|  | 25.8 |  | 7.9 |
|  | 27.1 |  | 21.0 |
| I—(CH₂)₃CH₃ | 6.1 |  | 12.3 |
| I—(CH₂)₅CH₃ | 4.3 |  | 4.7 |
| I—(CH₂)₂CH₃ | 2.6 |  | 4.4 |
|  | 2.7 |  | 2.6 |
|  | 2.7 |  | 2.6 |
| I—(CH₂)₂CH₃ | 3.8 |  | 1.4 |

TABLE A-continued

| Alkyl halide or tosylate | mass (g) | Alkoxy aryl product | mass (g) |
| --- | --- | --- | --- |
| CH₃—⟨C₆H₄⟩—SO₃—(CH₂)₂O(CH₂)₃CH₃ | 3.6 | CH₃(CH₂)₃O—(CH₂)₂O—⟨C₆H₄⟩—⟨C₆H₄⟩—C≡C—⟨C₆H₄⟩—CO₂CH₃ | 5.1 |
| CH₃—⟨C₆H₄⟩—SO₃—(CH₂)₂OC(CH₃)₃ | 4.9 | (CH₃)₃CO—(CH₂)₂O—⟨C₆H₄⟩—C≡C—⟨C₆H₄⟩—⟨C₆H₄⟩—CO₂CH₃ | 5.2 |

PREPARATION 2

The following nitrile and ester intermediates where $R_2$ is an alkoxy aryl moiety were prepared substantially in accordance with Procedure B, detailed above.

TABLE B

| Alkyl alcohol | mass (g) |
| --- | --- |
| HO—(CH₂)₂—N(piperidinyl)—(CH₂)₂CH₃ | 3.6 |
| HO—(CH₂)₂—N(piperidinyl)—CH₂—⟨C₆H₅⟩ | 6.1 |
| HO—(CH₂)₂—(piperidinyl)N—(CH₂)₅CH₃ | 0.5 |
| HO—(CH₂)₂—(piperidinyl)N—CH₂—⟨C₆H₁₁⟩ | 0.5 |
| HO—(CH₂)₂—N(piperidinyl)—⟨C₆H₁₁⟩ | 2.3 |
| HO—(CH₂)₂—N(piperidinyl)—CH₂—⟨C₆H₁₁⟩ | 9.3 |
| HO—CH₂—⟨C₆H₄⟩—(CH₂)₃CH₃ | 10.0 |

| Alkoxy Aryl Product | mass (g) |
| --- | --- |
| CH₃(CH₂)₂—(piperidinyl)N—(CH₂)₂O—⟨C₆H₄⟩—⟨C₆H₄⟩—CO₂CH₃ | 6.2 |
| ⟨C₆H₅⟩—CH₂—(piperidinyl)N—(CH₂)₂O—⟨C₆H₄⟩—⟨C₆H₄⟩—CO₂CH₃ | 4.3 |

TABLE B-continued

| Structure | Value |
|---|---|
| CH₃(CH₂)₅—N(piperidine-4-yl)—(CH₂)₂O—C₆H₄—C₆H₄—CO₂CH₃ | 0.8 |
| Cyclohexyl—CH₂—N(piperidine-4-yl)—(CH₂)₂O—C₆H₄—C₆H₄—CO₂CH₃ | 0.5 |
| Cyclohexyl—(piperidine-4-yl)N—(CH₂)₂O—C₆H₄—C₆H₄—CO₂CH₃ | 1.3 |
| Cyclohexyl—CH₂—(piperidine-3-yl)N—(CH₂)₂O—C₆H₄—C₆H₄—CO₂CH₃ | 9.6 |
| CH₃(CH₂)₃—C₆H₄—CH₂O—C₆H₄—CO₂CH₂CH₃ | 13.6 |

PREPARATION 3

The following ester intermediates where $R_2$ is an alkynyl or alkenyl aryl moiety were prepared substantially in accordance with Procedure C, detailed above.

TABLE C

| Alkene or alkyne | mass (g) | Aryl halide | mass (g) |
|---|---|---|---|
| $HC\equiv C-(CH_2)_5CH_3$ | 12.1 | I—C₆H₄—CO₂CH₃ | 28.8 |
| $HC\equiv C-(CH_2)_5CH_3$ | 6.1 | I—C₆H₄—CO₂CH₃ | 14.4 |
| $HC\equiv C-(CH_2)_7CH_3$ | 15.2 | I—C₆H₄—CO₂CH₃ | 28.8 |
| $HC\equiv C-C_6H_5$ | 1.9 | I—C₆H₄—CO₂CH₃ | 5.1 |
| $HC\equiv C-Si(CH_3)_3$ | 4.3 | I—C₆H₄—CO₂CH₃ | 11.5 |
| $HC\equiv C-C_6H_5$ | 1.8 | I—C₆H₄—C₆H₄—CO₂CH₃ | 6.0 |
| $HC\equiv C-(CH_2)_3CH_3$ | 1.4 | I—C₆H₄—C₆H₄—CO₂CH₃ | 6.0 |

TABLE C-continued

| | | | |
|---|---|---|---|
| HC≡C—Si(CH₃)₃ | 10.9 | I—⟨C₆H₄⟩—⟨C₆H₄⟩—CO₂CH₃ | 40.0 |
| HC≡C—(CH₂)₇CH₃ | 7.6 | Br—(furan)—CO₂CH₃ | 11.3 |
| HC≡C—⟨C₆H₄⟩—⟨C₆H₄⟩—CO₂CH₃ | 10.5 | I—⟨C₆H₄⟩—OH | 9.7 |
| HC≡C—⟨C₆H₄⟩—CO₂CH₃ | 22.2 | Br—⟨C₆H₄⟩—⟨C₆H₄⟩—OH | 34.4 |
| HC≡C—⟨C₆H₄⟩—⟨C₆H₄⟩—CO₂CH₃ | 1.2 | 2-bromofluorene | 1.2 |

| Alkenyl or alkynl aryl product | mass (g) |
|---|---|
| CH₃(CH₂)₅—C≡C—⟨C₆H₄⟩—CO₂CH₃ | 26.2 |
| (trans) CH₃(CH₂)₅—CH=CH—⟨C₆H₄⟩—CO₂CH₃ | 0.6 |
| CH₃(CH₂)₇—C≡C—⟨C₆H₄⟩—CO₂CH₃ | 28.1 |
| ⟨C₆H₅⟩—C≡C—⟨C₆H₄⟩—CO₂CH₃ | 1.9 |
| (CH₃)₃Si—C≡C—⟨C₆H₄⟩—CO₂CH₃ | 11.2 |
| ⟨C₆H₅⟩—C≡C—⟨C₆H₄⟩—⟨C₆H₄⟩—CO₂CH₃ | 2.6 |
| CH₃(CH₂)₃—C≡C—⟨C₆H₄⟩—⟨C₆H₄⟩—CO₂CH₃ | 5.1 |
| (CH₃)₃Si—C≡C—⟨C₆H₄⟩—⟨C₆H₄⟩—CO₂CH₃ | 23.3 |

TABLE C-continued
| Structure | Value |
|---|---|
| 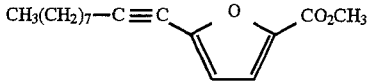 | 11.4 |
| 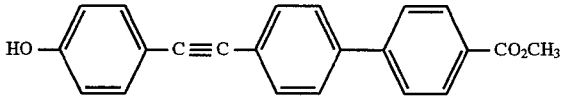 | 10.2 |
| 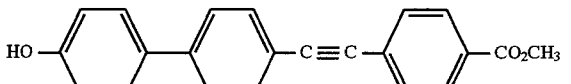 | 19.4 |
| 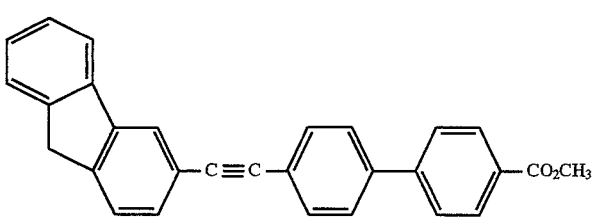 | 1.5 |
PREPARATION 4
The following ester intermediates where $R_2$ is a terphenyl moiety were prepared substantially in accordance with Procedure D, detailed above.
TABLE D1
| Aryl halide ($R^D$ is bromide) | mass (g) | Boronic acid reactant ($R^D$ is $B(OH)_2$) mass (g) |
|---|---|---|
| 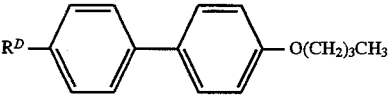 | 10.6 | 6.1 |
| 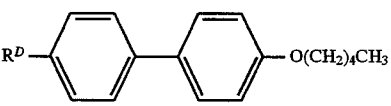 | 31.0 | 12.0 |
| 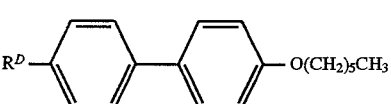 | 10.9 | 4.1 |
| 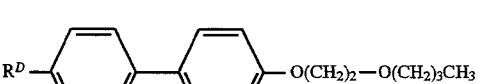 | 13.6 | 5.7 |
| 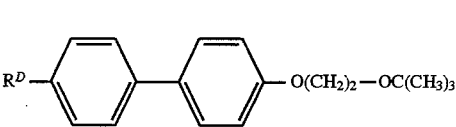 | 5.0 | 1.9 |

TABLE D2
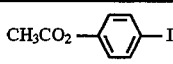
PREPARATION 5
The following activated esters were prepared substantially in accordance with Procedure G, detailed above.
TABLE G
| Carboxylic acid | mass (g) | mass (g) activated ester (2,4,5-trichlorophenyl ester) |
|---|---|---|
| CH₃(CH₂)₃O—⌬—⌬—COOH | 1.9 | 1.8 |
| ▱—CH₂O—⌬—⌬—COOH | 4.2 | 4.4 |
| (CH₃)₂CH(CH₂)₂O—⌬—⌬—COOH | 3.0 | 1.7 |
| CH₃(CH₂)₄O—(CH₂)₂O—⌬—⌬—COOH | 2.2 | 1.3 |

TABLE G-continued

| Carboxylic acid | mass (g) | mass (g) activated ester (2,4,5-trichlorophenyl ester) |
|---|---|---|
| $CH_3(CH_2)_4O$—〈C6H4〉—〈C6H4〉—COOH | 5.7 | 5.1 |
| cyclopentyl-$CH_2O$—〈C6H4〉—〈C6H4〉—COOH | 4.4 | 3.1 |
| $(CH_3)_3C(CH_2)_2O$—〈C6H4〉—〈C6H4〉—COOH | 2.3 | 2.6 |
| $(CH_3CH_2)_2CHCH_2O$—〈C6H4〉—〈C6H4〉—COOH | 1.5 | 0.8 |
| $CH_3(CH_2)_5O$—〈C6H4〉—〈C6H4〉—COOH | 5.3 | 4.8 |
| cyclohexyl-$(CH_2)_2O$—〈C6H4〉—〈C6H4〉—COOH | 3.1 | 1.0 |
| $CH_3(CH_2)_6O$—$(CH_2)_2O$—〈C6H4〉—COOH | 5.6 | 2.9 |
| $CH_3(CH_2)_7O$—$(CH_2)_2O$—〈C6H4〉—COOH | 7.8 | 6.6 |
| $CH_3(CH_2)_9O$—$(CH_2)_2O$—〈C6H4〉—COOH | 6.4 | 1.3 |
| $CH_3(CH_2)_3$—〈C6H4〉—$CH_2O$—〈C6H4〉—COOH | 4.0 | 3.2 |
| $CH_3(CH_2)_3O$—〈C6H4〉—O—〈C6H4〉—COOH | 5.8 | 1.4 |
| $CH_3(CH_2)_5O$—〈C6H4〉—O—〈C6H4〉—COOH | 3.8 | 2.4 |
| $CH_3(CH_2)_3O$—〈C6H4〉—〈C6H4〉—C≡C—〈C6H4〉—COOH | 2.9 | 2.5 |
| $CH_3(CH_2)_3O$—$(CH_2)_2O$—〈C6H4〉—〈C6H4〉—C≡C—〈C6H4〉—COOH | 2.0 | 1.5 |

TABLE G-continued

| Carboxylic acid | mass (g) | mass (g) activated ester (2,4,5-trichlorophenyl ester) |
|---|---|---|
| (CH₃)₃CO—(CH₂)₂O—⟨C₆H₄⟩—⟨C₆H₄⟩—C≡C—⟨C₆H₄⟩—COOH | 2.0 | 1.3 |
| CH₃(CH₂)₃O—⟨C₆H₄⟩—C≡C—⟨C₆H₄⟩—⟨C₆H₄⟩—COOH | 6.5 | 5.2 |
| CH₃(CH₂)₃O—(CH₂)₂O—⟨C₆H₄⟩—C≡C—⟨C₆H₄⟩—⟨C₆H₄⟩—COOH | 4.9 | 5.2 |
| (CH₃)₃CO—(CH₂)₂O—⟨C₆H₄⟩—C≡C—⟨C₆H₄⟩—⟨C₆H₄⟩—COOH | 4.6 | 2.1 |
| CH₃(CH₂)₂—⟨piperidine⟩—N—(CH₂)₂O—⟨C₆H₄⟩—⟨C₆H₄⟩—COOH | 3.3 | 1.5 |
| ⟨C₆H₅⟩—CH₂—⟨piperidine⟩—N—(CH₂)₂O—⟨C₆H₄⟩—⟨C₆H₄⟩—COOH | 3.0 | 2.3 |
| CH₃(CH₂)₅—N⟨piperidine⟩—(CH₂)₂O—⟨C₆H₄⟩—⟨C₆H₄⟩—COOH | 1.0 | 1.0 |
| ⟨C₆H₁₁⟩—CH₂—N⟨piperidine⟩—(CH₂)₂O—⟨C₆H₄⟩—⟨C₆H₄⟩—COOH | 2.0 | 0.8 |
| ⟨C₆H₁₁⟩—⟨piperidine⟩—N—(CH₂)₂O—⟨C₆H₄⟩—⟨C₆H₄⟩—COOH | 7.2 | 0.8 |
| ⟨C₆H₁₁⟩—CH₂—⟨piperidine⟩—N—(CH₂)₂O—⟨C₆H₄⟩—⟨C₆H₄⟩—COOH | 7.5 | 7.3 |
| ⟨C₆H₅⟩—C≡C—⟨C₆H₄⟩—⟨C₆H₄⟩—COOH | 2.0 | 0.6 |
| CH₃(CH₂)₃—C≡C—⟨C₆H₄⟩—⟨C₆H₄⟩—COOH | 1.1 | 0.6 |
| CH₃(CH₂)₅—C≡C—⟨C₆H₄⟩—COOH | 4.6 | 3.5 |
| (trans) CH₃(CH₂)₅—CH=C—⟨C₆H₄⟩—COOH | 1.2 | 0.5 |

TABLE G-continued

| Carboxylic acid | mass (g) | mass (g) activated ester (2,4,5-trichlorophenyl ester) |
|---|---|---|
| CH$_3$(CH$_2$)$_7$—C≡C—C$_6$H$_4$—C$_6$H$_4$—COOH | 11.1 | 13.2 |
| C$_6$H$_5$—C≡C—C$_6$H$_4$—COOH | 1.5 | 1.5 |
| CH$_3$(CH$_2$)$_7$—C≡C—(furan)—COOH | 8.3 | 13.2 |
| C$_6$H$_5$—C$_6$H$_4$—C$_6$H$_4$—COOH | 0.8 | 1.2 |
| CH$_3$(CH$_2$)$_3$O—C$_6$H$_4$—C$_6$H$_4$—C$_6$H$_4$—COOH | 3.3 | 4.8 |
| CH$_3$(CH$_2$)$_4$O—C$_6$H$_4$—C$_6$H$_4$—C$_6$H$_4$—COOH | 3.0 | 2.5 |
| CH$_3$(CH$_2$)$_5$O—C$_6$H$_4$—C$_6$H$_4$—C$_6$H$_4$—COOH | 2.3 | 3.9 |
| CH$_3$(CH$_2$)$_3$O—(CH$_2$)$_2$O—C$_6$H$_4$—C$_6$H$_4$—C$_6$H$_4$—COOH | 3.3 | 4.4 |
| (CH$_3$)$_3$CO—(CH$_2$)$_2$O—C$_6$H$_4$—C$_6$H$_4$—C$_6$H$_4$—COOH | 1.3 | 1.9 |

EXAMPLE 1

N-Acylation of Cyclic Peptide Nuclei

The N-acyl cyclic peptide derivatives listed in Table 2, below were prepared by dissolving Echinocandin B (A-30912A) nucleus (compound of formula IB where R', R" and R''' are each methyl, and $R^{x2}$, $R^{y1}$, $R^{y2}$, $R^{y3}$, $R^{y4}$ and $R_0$ are each hydroxy), and the activated ester (2,4,5-trichlorophenol ester) intermediates, described in Preparation 6, in 25–50 ml of dimethylformamide. The resultant reaction mixture was stirred for approximately 17–65 hours at room temperature and then the solvent was removed in vacuo to provide a residue. This residue was slurried in ether, collected by filtration, washed with methylene chloride and then dissolved in methanol or a 1:1 (v/v) acetonitrile/water mixture. The resultant solution is subjected to reverse phase HPLC (C18; eluent of 20–40% aqueous acetonitrile containing 0.5% monobasic ammonium phosphate (w/v); 20 ml/min.; 230 nm). After removing the unreacted A30912A nucleus, the desired product is eluted from the column using an eluent of aqueous acetonitrile. The fractions containing the desired product are combined and then concentrated in vacuo or lyophilized to provide the desired acylated nucleus. The purity (percentage) may be analyzed using reverse phase HPLC (C18; 40% aqueous acetonitrile containing 0.5% monobasic ammonium phosphate (w/v); 2 ml/min; 230 nm) and MS(FAB).

For example, the compound depicted in Table 2II, below, was prepared substantially according to this procedure, using 348.1 g (60.2 mmol) of the A30912A nucleus, 26.0 g (48.2 mmol) of the 2,4,5-trichlorophenol ester of [[(4"-pentyloxy)-1,1':4',1"-terphenyl]-4-carboxylic acid in 8.5 liter of dimethylformamide. The resultant reaction mixture was allowed to react for approximately forty eight hours and then concentrated in vacuo and purified using HPLC to provide 18 g of compound 2II.

MS (FAB): 1140.5103 ($M^{+1}$).

Compounds A-PP (listed in Table 2 below) were prepared substantially as described above.

TABLE 2

| Ex. No. | R₂ | | Ester (mg) | A30912A Nucleus (g) | Product (mg) | MS (FAB) | HPLC R$_T$ (min) |
|---|---|---|---|---|---|---|---|
| 2A | $CH_3(CH_2)_3O-$ | —⟨phenyl-phenyl⟩—C(O)— | 561 | 1.0 | 235 | 1072* | 4.08 |
| 2B | cyclobutyl-$CH_2O$ | —⟨phenyl-phenyl⟩—C(O)— | 576 | 1.0 | 294 | 1062* | 4.46 |
| 2C | $(CH_3)_2CH(CH_2)_2O-$ | —⟨phenyl-phenyl⟩—C(O)— | 579 | 1.0 | 355 | 1086* | 5.75 |
| 2D | $CH_3(CH_2)_4O-(CH_2)_2O-$ | —⟨phenyl-phenyl⟩—C(O)— | 634 | 1.0 | 359 | 1130* | 5.79 |
| 2E | $CH_3(CH_2)_4O-$ | —⟨phenyl-phenyl⟩—C(O)— | 289 | 0.5 | 81 | 1083* | 6.08 |
| 2F | cyclopentyl-$CH_2O$ | —⟨phenyl-phenyl⟩—C(O)— | 594 | 1.0 | 295 | 1098* | 6.44 |
| 2G | $(CH_3)_3C(CH_2)_2O-$ | —⟨phenyl-phenyl⟩—C(O)— | 596 | 1.0 | 270 | 1100* | 8.15 |
| 2H | $(CH_3CH_2)_2CHCH_2O-$ | —⟨phenyl-phenyl⟩—C(O)— | 596 | 1.0 | 359 | 1100* | 9.13 |
| 2I | $CH_3(CH_2)_5O-$ | —⟨phenyl-phenyl⟩—C(O)— | 596 | 1.0 | 301 | 1100* | 10.24 |

TABLE 2-continued

| Ex. No. | R₂ | Ester (mg) | A30912A Nucleus (g) | Product (mg) | MS (FAB) | HPLC R$_T$ (min) |
|---|---|---|---|---|---|---|
| 2J | CH₃(CH₂)₆O—(CH₂)₂O— with cyclohexyl-CH₂O— and biphenyl-C(O)— | 629 | 1.0 | 180 | 1104** | — |
| 2K | CH₃(CH₂)₆O—(CH₂)₂O— with phenyl-C(O)— | 287 | 0.5 | 110 | 1082* | 4.52 |
| 2L | CH₃(CH₂)₇O—(CH₂)₂O— with phenyl-C(O)— | 593 | 1.0 | 307 | 1096* | 7.28 |
| 2M | CH₃(CH₂)₉O—(CH₂)₂O— with phenyl-C(O)— | 313 | 0.5 | 104 | 1124* | 19.04 |
| 2N | CH₃(CH₂)₃ with phenyl-CH₂O-phenyl-C(O)— | 579 | 1.0 | 293 | 1032* | 6.14 |
| 2O | CH₃(CH₂)₃O— with phenyl-O-phenyl-C(O)— | 291 | 0.5 | 98 | 1088* | 3.96 |
| 2P | CH₃(CH₂)₅O— with phenyl-O-phenyl-C(O)— | 616 | 1.0 | 341 | 1116* | 11.56 |
| 2Q | CH₃(CH₂)₂O— with phenyl-C≡C-biphenyl-C(O)— | 2400 | 3.2 | 3000 | 1194.5213† | — |
| 2R | CH₃(CH₂)₃O—(CH₂)₂O— with phenyl-C≡C-biphenyl-C(O)— | 1300 | 1.5 | 2400 | 1194.5247† | — |

TABLE 2-continued

| Ex. No. | R₂ (structure) | Ester (mg) | A30912A Nucleus (g) | Product (mg) | MS (FAB) | HPLC R$_T$ (min) |
|---|---|---|---|---|---|---|
| 2S | (CH₃)₃CO—(CH₂)₂O— attached to terphenyl-C≡C—C(O)— | 4600 | 7.4 | 1300 | 1126.5025† | — |
| 2T | CH₃(CH₂)₂—N(piperidine-CH₂-phenyl)—(CH₂)₂O— biphenyl—C(O)— | 683 | 1.0 | 384 | 1147** | 1.92 |
| 2U | N(piperidine-CH₂-cyclohexyl)—(CH₂)₂O— biphenyl—C(O)— | 1490 | 2.0 | 116 | 1195** | 2.06 |
| 2V | CH₃(CH₂)₅—N(piperidine)—(CH₂)₂O— biphenyl—C(O)— | 1000 | 1.2 | 194 | 1190*** | 2.41 |
| 2W | piperidine-CH₂-cyclohexyl (CH₂)₂O biphenyl—C(O)— | 734 | 0.9 | 303 | 1202* | 2.21 |
| 2X | N(piperidine-CH₂-cyclohexyl)—(CH₂)₂O— biphenyl—C(O)— | 810 | 1.0 | 230 | 1187** | 2.52 |
| 2Y | N(piperidine-CH₂-cyclohexyl)—(CH₂)₂O— biphenyl—C(O)— | 750 | 1.0 | 126 | 1201** | 3.50 |
| 2Z | phenyl—C≡C— biphenyl—C(O)— | 596 | 1.0 | 190 | 1078** | 6.30 |
| 2AA | CH₃(CH₂)₃—C≡C— biphenyl—C(O)— | 571 | 1.0 | 295 | 1058** | 7.91 |

TABLE 2-continued

| Ex. No. | R₂ | Ester (mg) | A30912A Nucleus (g) | Product (mg) | MS (FAB) | HPLC R_T (min) |
|---|---|---|---|---|---|---|
| 2BB | CH₃(CH₂)₅—C≡C—[C₆H₄]—C(O)— | 511 | 1.0 | 322 | 1032* | 5.10 |
| 2CC | CH₃(CH₂)₅—CH=CH—[C₆H₄]—C(O)— (trans) | 514 | 1.0 | 287 | 1034* | 6.14 |
| 2DD | CH₃(CH₂)₇—C≡C—[C₆H₄—C₆H₄]—C(O)— | 546 | 1.0 | 285 | 1060* | 12.48 |
| 2EE | Ph—C≡C—[C₆H₄]—C(O)— | 501 | 1.0 | 218 | 1002** | 2.53 |
| 2FF | CH₃(CH₂)₇—C≡C—[furan-2,5-diyl]—C(O)— | 534 | 1.0 | 215 | 1050*** | 7.59 |
| 2GG | Ph—[C₆H₄]—[C₆H₄]—C(O)— | 566 | 1.0 | 81 | 1054** | 3.89 |
| 2HH | CH₃(CH₂)₄O—[C₆H₄]—[C₆H₄]—[C₆H₄]—C(O)— | 4600 | 7.4 | 1300 | 1126.5025† | — |
| 2II | CH₃(CH₂)₄O—[C₆H₄]—[C₆H₄]—[C₆H₄]—C(O)— | 2500 | 3.7 | 5100 | 1140.5103† | — |
| 2JJ | CH₃(CH₂)₅O—[C₆H₄]—[C₆H₄]—[C₆H₄]—C(O)— | 3500 | 5.0 | 1400 | 1154.5343†† | — |

TABLE 2-continued

| Ex. No. | R$_2$ | | Ester (mg) | A30912A Nucleus (g) | Product (mg) | MS (FAB) | HPLC R$_T$ (min) |
|---|---|---|---|---|---|---|---|
| 2KK | CH$_3$(CH$_2$)$_3$O—(CH$_2$)$_2$O | —[C$_6$H$_4$]—[C$_6$H$_4$]—[C$_6$H$_4$]—[C$_6$H$_4$]—C(O)— | 4000 | 6.7 | 6500 | 1170.5234† | — |
| 2LL | (CH$_3$)$_3$CO—(CH$_2$)$_2$O | —[C$_6$H$_4$]—[C$_6$H$_4$]—[C$_6$H$_4$]—[C$_6$H$_4$]—C(O)— | 1900 | 2.9 | 1400 | 1170.5261† | — |
| 2MM | CH$_3$(CH$_2$)$_3$O | —[C$_6$H$_4$]—C≡C—[C$_6$H$_4$]—[C$_6$H$_4$]—C(O)— | 5200 | 6.9 | 1400 | 1142.4951† | — |
| 2NN | (CH$_3$)$_3$CO—(CH$_2$)$_2$O | —[C$_6$H$_4$]—C≡C—[C$_6$H$_4$]—[C$_6$H$_4$]—[C$_6$H$_4$]—C(O)— | 2100 | 2.5 | 2000 | 1200.5336† | — |
| 2OO | CH$_3$(CH$_2$)$_3$O—(CH$_2$)$_2$O | —[C$_6$H$_4$]—C≡C—[C$_6$H$_4$]—[C$_6$H$_4$]—C(O)— | 5200 | 6.4 | 1100 | 1194.5282† | — |
| 2PP | | —[fluorenyl]—C≡C—[C$_6$H$_4$]—[C$_6$H$_4$]—C(O)— | 1800 | 2.6 | 200 | 1166.4758† | — |

*(m − 1) + [Na]†;
**(m + 1);
***m + [Na]†;
† m + 1;
†† m + [Li]†.

EXAMPLE 2

A. Preparation of the Compound where R', R" and R'" are each Methyl, $R^{x2}$, $R^{y1}$, $R^{y2}$, $R^{y3}$, $R^{y4}$ and $R_O$ are each Hydroxy, $R_2$ is the Acyl Group Depicted in Table 2Z and $R^{x1}$ is Prop-2-enyl To an anhydrous solution containing 0.1 g (0.09 mmol) of the compound depicted in Table 2Z and 631 μl (9 mmol) of 3-hydroxypropene in 10 ml of anhydrous dioxane, was added approximately 2 mg of p-toluenesulfonic acid. When the reaction was substantially complete, as indicated by thin layer chromatography (TLC), approximately 1 ml of a saturated sodium bicarbonate solution was added to the reaction mixture. The resultant mixture was concentrated in vacuo to provide a solid. This solid was washed on a fritted funnel with water and then removed using methanol and the resulting mixture was purified using reverse phase preparative HPLC (eluent of 60% aqueous acetonitrile, 75 ml/min.; 290 nm) to provide 88 mg of a white powder.

B. Preparation of the Compound where R', R" and R'" are each Methyl, $R^{x2}$, $R^{y1}$, $R^{y2}$, $R^{y3}$, $R^{y4}$ and $R_O$ are each Hydroxy, $R_2$ is the Acyl Group Depicted in Table 2Z and $R^{x1}$ is 2,3-dihydroxypropyl To a cold (0° C.) solution of the compound of Example 2A in a 1:1 mixture of dioxane and water, was added 4-methylmorpholine 4-oxide monohydrate (NMO) followed by osmium tetroxide. An excess of sodium meta-bisulfite was added and the resultant mixture was allowed to react for approximately five hours. The reaction mixture was allowed to warm to room temperature and then reacted for approximately sixteen hours. The resultant mixture was filtered and the filtrate was concentrated in vacuo to provide a residue. This residue was redissolved in methanol and then filtered through a fritted glass funnel. The filtrate was concentrated in vacuo to provide a residue. This residue was redissolved in a methanol/acetonitrile/water mixture and the desired compound was isolated using reverse phase preparative HPLC (eluent of 60% aqueous acetonitrile, 75 ml/min.; 290 nm).

Yield: 21 mg. MS(FAB): Calcd: 1152.4777; Found: 1152.4826

EXAMPLE 3

A. Preparation of the Compound where R', R" and R'" are each Methyl, $R^{x2}$, $R^{y1}$, $R^{y2}$, $R^{y3}$, $R^{y4}$ and $R_O$ are each Hydroxy, $R_2$ is the Acyl Group Depicted in Table 2II and $R^{x1}$ is Prop-2-enyl The subtitled compound was prepared substantially in accordance with the procedure detailed in Example 2A, using 1.0 g (0.88 mmol) of the compound depicted in Table 2II, 5.0 g (86.2 mmol) of 3-hydroxypropene and 8.3 mg (0.044 mmol) of p-toluenesulfonic acid (5 mol percent) in 100 ml of anhydrous dioxane.

MS(FAB): 1186.5 (M+Li).

B. Preparation of the Compound where R', R" and R'" are each Methyl, $R^{x2}$, $R^{y1}$, $R^{y2}$, $R^{y3}$, $R^{y4}$ and $R_O$ are each Hydroxy, $R_2$ is the Acyl Group Depicted in Table 2II and $R^{x1}$ is 2,3-dihyroxypropyl The subtitled compound was prepared substantially in accordance with the procedure detailed in Example 2B, using the compound of Example 3A, a catalytic amount of osmium tetroxide and 4-methylmorpholine 4-oxide monohydrate in a 1:1 mixture of dioxane and water. The desired compound was isolated using reverse phase preparative HPLC (eluent of 45% aqueous acetonitrile, 50 ml/min.; 290 nm).

Yield: 200 mg. MS(FAB): 1235.5 (M+Na).

EXAMPLE 4

A. Preparation of the Compound where R', R" and R'" are each Methyl, $R^{x2}$, $R^{y1}$, $R^{y2}$, $R^{y3}$, $R^{y4}$ and $R_O$ are each Hydroxy, $R_2$ is the Acyl Group depicted in Table 2II and $R^{x1}$ is 4-(benzyloxycarbonylamino)butyl To a solution containing 557.2 mg (0.501 mmol) of the compound depicted in Table 2II and 1.1188 g (5.02 mmol) of 4-(benzyloxycarbonylamino)butanol in 50 ml of dioxane, was added a catalytic amount (approximately 10 mol percent) of p-toluenesulfonic acid. When the reaction was substantially complete, as indicated by HPLC, the reaction was quenched with solid sodium bicarbonate. The resultant reaction mixture was concentrated in vacuo to provide a solid which was used without further purification.

MS(FAB): 1368.1 (M+Na).

B. Preparation of the Compound where R', R" and R'" are each Methyl, $R^{x2}$, $R^{y1}$, $B^{y2}$, $R^{y3}$, $R^{y4}$ and $R_O$ are each Hydroxy, $R_2$ is the Acyl Group Depicted in Table 2II and $R^{x1}$ is 4-aminobutyl To a mixture of the compound from Example 4A in a 1:1 mixture of methanol and water, was added a catalytic amount (10 mol percent) of 10% palladium-on-carbon and two drops of glacial acetic acid. The resultant reaction was allowed to react under 1 atmosphere of hydrogen (gas). When the reaction was substantially complete, as indicated by HPLC, the reaction mixture was filtered. The filtrate was concentrated in vacuo to provide the desired subtitled compound.

Yield: 78 mg. MS(FAB): 1211.5 (M+).

EXAMPLE 5

A. Preparation of the Compound where R', R" and R'" are each Methyl, $R^{x2}$, $R^{y1}$, $R^{y2}$, $R^{y3}$, $R^{y4}$ and $R_O$ are each Hydroxy, $R_2$ is the Acyl Group Depicted in Table 2II and $R^{x1}$ is 6-(benzyloxycarbonylamino)hexyl The desired subtitled compound was prepared substantially in accordance with the procedure detailed in Example 4A, using 553.2 mg (0.497 mmol) of the compound depicted in Table 2II, 1.1190 g (4.458 mmol) of 6-(benzyloxycarbonylamino)hexanol and a catalytic amount (approximately 10 mol percent) of p-toluenesulfonic acid in 50 ml of dioxane to provide a solid which was used without further purification.

MS(FAB): 1395.7 (M+Na).

B. Preparation of the Compound where R', R" and R'" are each Methyl, $R^{x2}$, $R^{y1}$, $R^{y2}$, $R^{y3}$, $R^{y4}$ and $R_O$ are each hydroxy, $R_2$ is the Acyl Group Depicted in Table 2II and $R^{x1}$ is 6-aminohexyl The desired subtitled compound was prepared substantially in accordance with the procedure detailed in Example 4A, using the compound from Example 5A, a catalytic amount (10 mol percent) of 10% palladium-on-carbon, and two drops of glacial acetic acid in a 1:1 mixture of methanol and water, under 1 atmosphere of hydrogen (gas).

Yield: 102 mg. MS(FAB): 1361.7 (M+Na).

EXAMPLE 6

Preparation of the Compound where R', R" and R'" are each Methyl, $R^{x2}$, $R^{y1}$, $R^{y2}$, $R^{y3}$, $R^{y4}$ and $R_0$ are each Hydroxy, $R_2$ is the Acyl Group Depicted in Table 2II and $R^{x1}$ is Carboxymethyl A solution containing 2.00 g (1.75 mmol) of the compound depicted in Table 2II, 2.668 g (35.08 mmol) of glycolic acid, and 66 mg (0.350 mmol) of p-toluenesulfonic acid in 40 ml of dioxane was allowed to react at room temperature. When the reaction was substantially complete, as indicated by TLC, the reaction mixture was filtered and the resultant filtrate was applied to a reverse phase preparative HPLC column (eluent of 50% aqueous acetonitrile containing 0.1% trifluoroacetic acid; 80 ml/min.; 280 nm). The fractions containing the desired compound were combined and concentrated in vacuo to provide 0.770 g of an off-white solid which was determined to be 86.5% pure using HPLC (C18; eluent of 55% aqueous acetonitrile containing 0.1% trifluoroacetic acid, 2 ml/min.; 280 nm; $R_T$=4.13 min.).

Yield: 37%. MS(FAB): 1162.7 (M-2H$_2$O)

EXAMPLE 7

Preparation of the Compound where R', R" and R'" are each Methyl, $R^{x2}$, $R^{y1}$, $R^{y2}$, $R^{y3}$, $R^{y4}$ and $R_0$ are each Hydroxy, $R_2$ is the Acyl Group Depicted in Table 2II and $R^{x1}$ is Carboxymethyl, Sodium Salt To a suspension of 0.3 g (0.25 mmol) of the compound of Example 6 in 5 ml of water, was added 0.25 ml of 1N sodium hydroxide (0.25 mmol). The resultant reaction mixture was slowly heated until the solid went into solution. The resultant solution was lyophilized to provide 236 mg of the desired titled compound.

MS(FAB): 1221.7 (M$^+$)

EXAMPLE 8

Preparation of the Compound where R', R" and R'" are each Methyl, $R^{x2}$, $R^{y1}$, $R^{y2}$, $R^{y3}$, $R^{y4}$ and $R_0$ are each hydroxy, $R_2$ is the Acyl Group Depicted in Table 2II and $R^{x1}$ is Methyl To a solution of 400 mg of the compound depicted in Table 2II in 30 ml of methanol, was added approximately 1 ml of 1N hydrochloric acid. When the reaction was substantially complete, as determined by HPLC (eluent of 50% aqueous acetonitrile; 2 ml/min.; 280 nm), the reaction mixture was applied to a preparative HPLC column (eluent of 50% aqueous acetonitrile, 90 ml/min.; 280 nm). The fractions containing the desired compound were combined and concentrated in vacuo to provide 223.7 mg of the titled compound which was determined to be 98.7% pure using HPLC (eluent of 50% aqueous acetonitrile; 2 ml/min.; 280 nm; $R_T$=8.55 min.).

MS(FAB) for C$_{59}$H$_{75}$N$_7$O$_{17}$Na. Calcd: 1176.5117 (M+Na); Found: 1176.5140.

EXAMPLE 9

Preparation of the Compound where R', R" and R'" are each Methyl, $R^{x2}$, $R^{y1}$, $R^{y2}$, $R^{y3}$, $R^{y4}$ and $R_0$ are each Hydroxy, $R_2$ is the Acyl Group Depicted in Table 2II and $R^{x1}$ is 2-aminoethyl, Hydrochloride Salt A stream of hydrochloric acid (gas) was briefly passed over the surface of a solution containing 1.0 g (0.88 mmol) of the compound depicted in Table 2II and 1.71 g (88.0 mmol) of ethanolamine hydrochloride in 15 ml of dimethylsulfoxide. The resultant reaction mixture was allowed to react for approximately ninety six hours. When the reaction was substantially complete, as indicated by HPLC (C18; eluent of 50% aqueous acetonitrile containing 0.5% monobasic ammonium phosphate; 2 ml/min, 280 nm), the desired compound was isolated using preparative HPLC (C18; eluent of 45% aqueous acetonitrile containing 0.1% trifluoroacetic acid; 90 ml/min). The fractions containing the desired compound were combined and concentrated in vacuo to provide 490 mg which was determined to be 96% pure using HPLC (C18; eluent of 50% aqueous acetonitrile containing 0.5% monobasic ammonium phosphate; 2 ml/min.; $R_T$=2.96 min.).

Yield: 43%. MS (FAB): 1183 (M$^+$).

EXAMPLE 10

Preparation of the Compound where R', R" and R'" are each Methyl, $R^{x2}$, $R^{y1}$, $R^{y2}$, $R^{y3}$, $R^{y4}$ and $R_0$ are each Hydroxy, $R_2$ is the Acyl Group Depicted in Table 2II and $R^{x1}$ is Ethylphosphonic Acid, Dimethylester To a mixture containing 1 g (0.88 mmol) of the compound depicted in Table 2II and 11 ml (88 mmol) of dimethyl-2-hydroxyethylphosphonate in 10 ml of dioxane, was added 17 mg (0.088 mmol) of p-toluenesulfonic acid. The resultant reaction mixture was allowed to react for approximately twenty three hours. When the reaction was substantially complete, as indicated by HPLC (C18; eluent of 50% aqueous acetonitrile; 2 ml/min, 280 nm), the desired compound was isolated using preparative reverse phase HPLC (C18; gradient eluent of 45–48% aqueous acetonitrile; 90 ml/min). The fractions containing the desired compound were combined and concentrated in vacuo to provide 753 mg which was determined to be 94% pure using HPLC (C18; eluent of 50% aqueous acetonitrile; 2 ml/min, 280 nm; $R_T$=7.2 min.).

Yield: 67%. MS(FAB) for C$_{62}$H$_{82}$N$_7$O$_{20}$PNa. Calcd: 1298.5250 (M+Na); Found: 1298.5281.

EXAMPLE 11

Preparation of the Compound where R', R" and R'" are each Methyl, $R^{x2}$, $R^{y1}$, $R^{y2}$, $R^{y3}$, $R^{y4}$ and $R_0$ are each hydroxy, $R_2$ is the Acyl Group Depicted in Table 2II, and $R^{x1}$ is Ethylphosphonic Acid, Monomethylester A solution of 22.5 mg (0.936 mmol) of lithium hydroxide in 2 ml of water was added to a slurry of 200 mg (0.156 mmol) of the titled compound of Example 10 in 5 ml of dioxane. The resultant reaction mixture was allowed to react for approximately 6.5 hours. When the reaction was substantially complete, as indicated by HPLC (C18; eluent of 50% aqueous acetonitrile containing 0.5% monobasic ammonium phosphate; 2 ml/min, 280 nm), the desired compound was isolated using preparative HPLC (C18; eluent of 40% aqueous acetonitrile, 90 ml/min., 280 nm). The fractions containing the desired compound were combined and concentrated in vacuo to provide 43 mg which was determined to be 98% pure using HPLC (C18; eluent of 45% aqueous acetonitrile containing 0.5% monobasic ammonium phosphate; 2 ml/min, 280 nm; $R_T$=4.47 min.).

Yield: 22%. MS(FAB) for C$_{61}$H$_{80}$N$_7$O$_{20}$PLi. Calcd: 1268.5356 (M+Li); Found: 1268.5403.

EXAMPLE 12

Preparation of the Compound where R', R" and R'"
are each Methyl, $R^{x2}$, $R^{y1}$, $R^{y2}$, $R^{y3}$, $R^{y4}$ and $R_0$ are
each hydroxy, $R_2$ is the Acyl Group Depicted in
Table 2II, and $R^{x1}$ is 2-(2-ethoxyethoxy)ethyl A solution containing 1.00 mg (0.877 mmol) of the compound depicted in Table 2II, 11.780 ml (87.690 mmol) of 2-(2-ethoxyethoxy)ethanol, and 0.34 g (0.175 mmol) of p-toluenesulfonic acid in 20 ml of dioxane was allowed to react for approximately thirty six hours. When the reaction was substantially complete, as indicated by TLC, 6.48 g (0.0876 mmol) of sodium bicarbonate was added to the reaction and the resultant mixture was concentrated in vacuo to provide 0.160 g of a white solid which was determined to be 99.6% pure using HPLC (C18; eluent of 65% aqueous acetonitrile containing 0.5% monobasic ammonium phosphate; 2 ml/min, 280 nm; $R_T$=3.58 min.).

Yield: 14%. MS(FAB) for $C_{64}H_{85}N_7O_{19}Li$: Calcd: 1262.6060 (M+Li); Found: 1262.6074

EXAMPLE 13

A. 2-(N-methyl-N-butylamino)ethanol Hydrochloride

Hydrochloric acid (gas) was bubbled through a solution of 10.0 g (0.0762 mmol) of 2-(N-methyl-N-butylamino) ethanol in diethyl ether. The resultant solution was concentrated in vacuo to provide a gold oil.

B. Preparation of the Compound where R', R" and R'" are each Methyl, $R^{x2}$, $R^{y1}$, $R^{y2}$, $R^{y3}$, $R^{y4}$ and $R_0$ are each Hydroxy, $R_2$ is the Acyl Group Depicted in Table 2II and $R^{x1}$ is 2-(N-methyl-N-butylamino) ethyl To a solution of the oil isolated in Example 13A in 100 ml of dimethylsulfoxide, was added 1.00 g (0.877 mmol) of the compound depicted in Table 2II. A stream of hydrochloric acid (gas) was briefly passed over the surface of the solution and then the resultant reaction mixture was allowed to react for approximately one week. When the reaction was substantially complete, as indicated by HPLC (eluent of 50% aqueous acetonitrile containing 0.1% trifluoroacetic acid), the reaction mixture was filtered. The resultant filtrate was applied to a preparatory HPLC column (eluent of 50% aqueous acetonitrile containing 0.1% trifluoroacetic acid; 80 ml/min.; 280 nm). The fractions containing the desired compound were combined and concentrated in vacuo to provide 40 mg of a white fluffy solid which was determined to be 85.6% pure using HPLC (C18; eluent of 50% aqueous acetonitrile containing 0.1% trifluoroacetic acid; 2 ml/min.; 280 nm; $R_T$=4.75 min.).

Yield: 3.7%. MS(FAB) for $C_{56}H_{89}N_8O_{17}$: Calcd: 1253.6346 (M); Found: 1253.6393.

EXAMPLE 14

Preparation of the Compound where R', R" and R'"
are each Methyl, $R^{x2}$, $R^{y1}$, $R^{y2}$, $R^{y3}$, $R^{y4}$ and $R_0$ are
each Hydroxy, $R_2$ is the Acyl Group Depicted in
Table 2II and $R^{x1}$ is 2-(N,N-dimethylamino)ethyl The titled compound was prepared substantially in accordance with the procedures detailed in Examples 13A and 13B, using 17.63 ml (175.39 mmol) of 2-(N,N-dimethylamino)ethanol, 2.00 g (1.75 mmol) of the compound depicted in Table 2II, and hydrochloric acid (gas) to provide 0.559 g of a white fluffy solid which was determined to be 99.9% pure using HPLC (C18; eluent of 50% aqueous acetonitrile containing 0.1% trifluoroacetic acid; 2 ml/min.; 280 nm; $R_T$=5.39 min.).

Yield: 26%. MS(FAB) for $C_{62}H_{83}N_8O_{17}$. Calcd: 1211.5876 (M); Found: 1211.5883.

EXAMPLE 15

Preparation of the Compound where R', R" and R'"
are each Methyl, $R^{x2}$, $R^{y1}$, $R^{y2}$, $R^{y3}$, $R^{y4}$ and $R_0$ are
each Hydroxy, $R_2$ is the Acyl Group Depicted in
Table 2II and $R^{x1}$ is 2-pyrrolidin-1-ylethyl The titled compound was prepared substantially in accordance with the procedures detailed in Examples 13A and 13B, using 20.51 ml (175.39 mmol) of 1-(2-hydroxyethyl) pyrrolidine, 2.00 g (1.75 mmol) of the compound depicted in Table 2II, and hydrochloric acid (gas) to provide 363 mg of a white fluffy solid which was determined to be 96.8% pure using HPLC (C18; eluent of 55% aqueous acetonitrile containing 0.1% trifluoroacetic acid; 2 ml/min.; 280 nm; $R_T$=3.84 min.).

Yield: 17%. MS (FAB) for $C_{64}H_{85}N_8O_{17}$. Calcd: 1237.6033 (M); Found: 1237.5991.

EXAMPLE 16

Preparation of the Compound where R', R" and R'"
are each Methyl, $R^{x2}$, $R^{y1}$, $R^{y2}$, $R^{y3}$, $R^{y4}$ and $R_0$ are
each Hydroxy, $R_2$ is the Acyl Group Depicted in
Table 2II and $R^{x1}$ is 2-(N-methyl-N-ethylamino) ethyl The titled compound was prepared substantially in accordance with the procedures detailed in Examples 13A and 13B, using 20 ml (175.39 mmol) of N,N-dimethylethanolamine, 2.00 g (1.75 mmol) of the compound depicted in Table 2II, and hydrochloric acid (gas) to provide 0.975 g of a white fluffy solid which was determined to be 97.3% pure using HPLC (C18; eluent of 50% aqueous acetonitrile containing 0.1% trifluoroacetic acid; 2 ml/min.; 280 nm; $R_T$=4.8 min.).

Yield: 46%. MS(FAB) for $C_{63}H_{85}N_8O_{17}$. Calcd: 1225.6033 (M); Found: 1225.5995.

EXAMPLE 17

Preparation of the Compound where R', R" and R'"
are each Methyl, $R^{x2}$, $R^{y1}$, $R^{y2}$, $R^{y3}$, $R^{y4}$ and $R_0$ are
each Hydroxy, $R_2$ is the Acyl Group Depicted in
Table 2II and $R^{x1}$ is Benzyl The desired compound was prepared substantially in accordance with the procedure detailed in Example 4A, using 750 mg (0.658 mmol) of the compound depicted in Table 2II, 3.404 ml (32.89 mmol) of benzylic alcohol, and a catalytic amount (approximately 10 mol percent) of p-toluenesulfonic acid in 50 ml of dioxane.

MS(FAB) for $C_{65}H_{80}N_7O_{17}$. Calcd: 1230.5611 (M$^+$); Found: 1230.5650.

EXAMPLE 18

Preparation of the Compound where R', R" and R'"
are each Methyl, $R^{x2}$, $R^{y1}$, $R^{y2}$, $R^{y3}$, $R^{y4}$ and $R_0$ are
each Hydroxy, $R_2$ is the Acyl Group Depicted in
Table 2II and $R^{x1}$ is 2-(trimethylsilyl)ethyl To a solution of 2.5 g (1.8 mmol) of the compound of Table 2II and 25 ml (175 mmol) of 2-(trimethylsilyl)ethanol in 50 ml of dioxane at room temperature, was added a catalytic amount of p-toluenesulfonic acid. The resultant reaction mixture was allowed to react at room temperature for approximately seven hours. When the reaction was substantially complete, as indicated by HPLC, the reaction was quenched with solid sodium bicarbonate and filtered. The desired titled compound was isolated from the filtrate using reverse phase HPLC (50% acetonitrile/50% water; 50 ml/min.; 280 nm).

MS(FAB): 1262.7 (M+Na)

The compounds of formula I exhibit antifungal and antiparasitic activity. For example, the compounds of formula I inhibit the growth of various infectious fungi including Candida spp. such as *C. albicans, C. parapsilosis, C. krusei, C. glabrata*, or *C. tropicalis, C. lusitaniae;* Torulopus spp. such as *T. glabrata;* Aspergillus spp. such as *A. fumigatus;* Histoplasma spp. such as *H. capsulatum;* Cryptococcus spp. such as *C. neoformans;* Blastomyces spp. such as *B. dermatitidis;* Fusarium spp., Trichophyton spp., *Pseudallescheria boydii, Coccidioides immitis, Sporothrix schenckii* and the like.

Antifungal activity of a test compound is determined in vitro by obtaining the minimum inhibitory concentration (MIC) of the compound using a standard agar dilution test or a disc-diffusion test. The compound is then tested in vivo (in mice) to determine the effective dose of the test compound for controlling a systemic fungal infection.

Accordingly, the following compounds were tested for antifungal activity against *C. albicans*.

TABLE 3

| Minimal inhibitory concentration against *C. albicans* | |
|---|---|
| Example | MIC (μg/ml) |
| 2B | 0.039 |
| 3B | 0.0098 |
| 4B | 0.312 |
| 5B | 0.312 |
| 6 | 0.078 |
| 7 | 0.039 |
| 8 | 0.005 |
| 9 | 0.020 |
| 10 | 0.020 |
| 11 | 0.039 |
| 12 | 0.156 |
| 13 | 0.625 |
| 14 | 0.156 |
| 15 | 0.312 |
| 16 | 0.156 |
| 17 | N.T. |
| 18 | 0.25 |

N.T. not tested.

In addition, the effective dose of the following compounds for controlling a systemic fungal infection (*C. albicans*) was tested in vivo mice).

TABLE 4

| $ED_{50}$ (mouse, i.p.) | |
|---|---|
| Example No. | $ED_{50}$ (mg/kg) |
| 2B | N.T. |
| 3B | |
| 4B | 1.25 |
| 5B | 1.67 |
| 6 | >2.5 |
| 7 | 1.38 |
| 8 | 0.99 |

TABLE 4-continued

| $ED_{50}$ (mouse, i.p.) | |
|---|---|
| Example No. | $ED_{50}$ (mg/kg) |
| 9 | 0.312 |
| 10 | 1.25 |
| 11 | 1.13 |
| 12 | >2.5 |
| 13 | 0.47 |
| 14 | 0.312 |
| 15 | 0.34 |
| 16 | 0.34 |
| 17 | N.T. |
| 18 | >2.5 |

N.T. not tested.

The compounds of the invention also inhibit the growth of certain organisms primarily responsible for opportunistic infections in immunosuppressed individuals. For example the compounds of the invention inhibit the growth of *Pneumocystis carinii* the causative organism of pneumocystis pneumonia (PCP) in AIDS and other immunocompromised patients. Other protozoans that are inhibited by compounds of formula I include Plasmodium spp., Leishmania spp., Trypanosoma spp., Cryptosporidium spp., Isospora spp., Cyclospora spp., Trichomonas spp., Microsporidiosis spp. and the like.

The compounds of formula I are active in vitro and in vivo and are useful in combating either systemic fungal infections or fungal skin infections. Accordingly, the present invention provides a method of inhibiting fungal activity comprising contacting a compound of formula I, or a pharmaceutically acceptable salt thereof, with a fungus. A preferred method includes inhibiting *Candida albicans* or *Aspergillus fumigatis* activity. The present invention further provides a method of treating a fungal infection which comprises administering an effective amount of a compound of formula I, or a pharmaceutically acceptable salt thereof, to a host in need of such treatment. A preferred method includes treating a *Candida albicans* or *Aspergillus fumigatis* infection.

With respect to antifungal activity, the term "effective amount," means an amount of a compound of the present invention which is capable of inhibiting fungal activity. The dose administered will vary depending on such factors as the nature and severity of the infection, the age and general health of the host and the tolerance of the host to the antifungal agent. The particular dose regimen likewise may vary according to such factors and may be given in a single daily dose or in multiple doses during the day. The regimen may last from about 2-3 days to about 2-3 weeks or longer. A typical daily dose (administered in single or divided doses) will contain a dosage level of from about 0.01 mg/kg to about 100 mg/kg of body weight of an active compound of this invention. Preferred daily doses generally will be from about 0.1 mg/kg to about 60 mg/kg and ideally from about 2.5 mg/kg to about 40 mg/kg.

The present invention also provides pharmaceutical formulations useful for administering the antifungal compounds of the invention. Accordingly, the present invention also provides a pharmaceutical formulation comprising one or more pharmaceutically acceptable carriers, diluents or excipients and a compound of claim 1. The active ingredient in such formulations comprises from 0.1% to 99.9% by weight of the formulation, more generally from about 10% to about 30% by weight. By "pharmaceutically acceptable" it is meant that the carrier, diluent or excipient is compatible with the other ingredients of the formulation and not deleterious to the recipient thereof.

A compound of formula I may be administered parenterally, for example using intramuscular, subcutaneous, or intra-peritoneal injection, nasal, or oral means. In addition to these methods of administration, a compound of formula I may be applied topically for skin infections.

For parenteral administration the formulation comprises a compound of formula I and a physiologically acceptable diluent such as deionized water, physiological saline, 5% dextrose and other commonly used diluents. The formulation may contain a solubilizing agent such as a polyethylene glycol or polypropylene glycol or other known solubilizing agent. Such formulations may be made up in sterile vials containing the antifungal and excipient in a dry powder or lyophilized powder form. Prior to use, a physiologically acceptable diluent is added and the solution withdrawn via syringe for administration to the patient.

The present pharmaceutical formulations are prepared by known procedures using known and readily available ingredients. In making the compositions of the present invention, the active ingredient will generally be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols, (as a solid or in a liquid medium), ointments containing, for example, up to 10% by weight of the active compound, soft and hard gelatin capsules, suppositories, sterile injectable solutions, sterile packaged powders and the like.

For oral administration, the antifungal compound is filled into gelatin capsules or formed into tablets. Such tablets may also contain a binding agent, a dispersant or other suitable excipients suitable for preparing a proper size tablet for the dosage and particular antifungal compound of the formula I. For pediatric or geriatric use the antifungal compound may be formulated into a flavored liquid suspension, solution or emulsion. A preferred oral formulation is linoleic acid, cremophor RH-60 and water and preferably in the amount (by volume) of 8% linoleic acid, 5% cremophor RH-60, 87% sterile water and a compound of formula I in an amount of from about 2.5 to about 40 mg/ml.

For topical use the antifungal compound may be formulated with a dry powder for application to the skin surface or it may be formulated in a liquid formulation comprising a solubilizing aqueous liquid or non-aqueous liquid, e.g., an alcohol or glycol.

The following formulation examples are illustrative only and are not intended to limit the scope of the invention in any way. The term "active ingredient" means a compound according to formula I or a pharmaceutically acceptable salt thereof.

FORMULATION 1

Hard gelatin capsules are prepared using the following ingredients:

|  | Quantity (mg/capsule) |
| --- | --- |
| Active ingredient | 250 |
| Starch, dried | 200 |
| Magnesium stearate | 10 |
| Total | 460 mg |

FORMULATION 2

A tablet is prepared using the ingredients below:

|  | Quantity (mg/capsule) |
| --- | --- |
| Active ingredient | 250 |
| Cellulose, microcrystalline | 400 |
| Silicon dioxide, fumed | 10 |
| Stearic acid | 13 |
| Total | 665 mg |

The components are blended and compressed to form tablets each weighing 665 mg.

FORMULATION 3

An aerosol solution is prepared containing the following components:

|  | Weight |
| --- | --- |
| Active ingredient | 0.25 |
| Methanol | 25.75 |
| Propellant 22 (Chlorodifluoromethane) | 74.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

FORMULATION 4

Tablets, each containing 60 mg of active ingredient, are made as follows:

| Active ingredient | 60 mg |
| --- | --- |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The aqueous solution containing polyvinyl-pyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

FORMULATION 5

Capsules, each containing 80 mg of active ingredient, are made as follows:

| Active ingredient | 80 mg |
|---|---|
| Starch | 59 mg |
| Microcrystalline cellulose | 59 mg |
| Magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities.

FORMULATION 6

Suppositories, each containing 225 mg of active ingredient, are made as follows:

| Active ingredient | 225 mg |
|---|---|
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

FORMULATION 7

Suspensions, each containing 50 mg of active ingredient per 5 ml dose, are made as follows:

| Active ingredient | 50 mg |
|---|---|
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

FORMULATION 8

An intravenous formulation may be prepared as follows:

| Active ingredient | 100 mg |
|---|---|
| Isotonic saline | 1,000 ml |

The solution of the above ingredients generally is administered intravenously to a subject at a rate of 1 ml per minute.

The present invention further provides a method for treating or preventing the onset of Pneumocystis pneumonia in a host susceptible to Pneumocystis pneumonia which comprises administering an effective amount of a compound of formula I, or a pharmaceutically acceptable salt thereof, to a host in need of such treatment. The compounds of formula I can be used prophylactically to prevent the onset of the infection which is caused by the organism Pneumocystis carinii, or alternatively they can be used to treat a host that has been infected with P. carinii. A compound of formula I may be administered parenterally, for example using intramuscular, intravenous or intra-peritoneal injection, orally or by inhaling directly into the airways of the lungs. A preferred mode of administration is inhalation of an aerosol spray formulation of a compound of formula I.

With respect to antiparasitic activity, the term "effective amount," means an amount of a compound of the present invention which is capable of inhibiting parasitic activity. An effective amount of the compound of formula I is from about 3 mg/kg of patient body weight to about 100 mg/kg. The amount administered may be in a single daily dose or multiple doses of, for example, two, three or four times daily throughout the treatment regimen. The amount of the individual doses, the route of delivery, the frequency of dosing and the term of therapy will vary according to such factors as the intensity and extent of infection, the age and general health of the patient, the response of the patient to therapy and how well the patient tolerates the drug. It is known that Pneumocystis pneumonia infections in AIDS patients are highly refractory owing to the nature of the infection. For example, in severe, advanced infections the lumenal surface of the air passages becomes clogged with infectious matter and extensive parasite development occurs in lung tissue. A patient with an advanced infection will accordingly require higher doses for longer periods of time. In contrast, immune deficient patients who are not severely infected and who are susceptible to Pneumocystis pneumonia can be treated with lower and less frequent prophylactic doses.

We claim:

1. A compound of formula I:

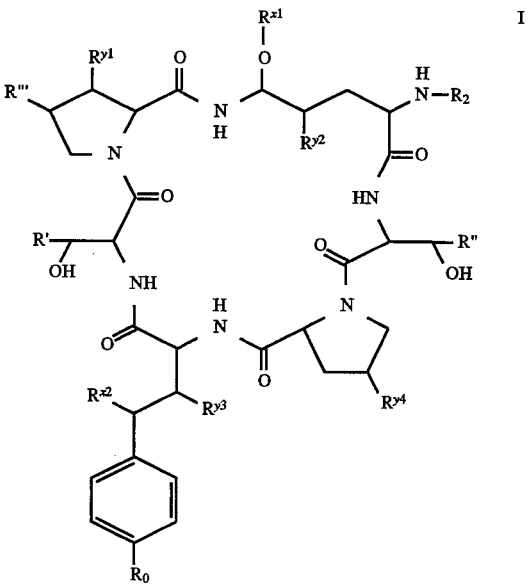

wherein:

R' is hydrogen, methyl or —$CH_2C(O)NH_2$;

R" and R''' are independently hydrogen or methyl;

$R^{x1}$ is $C_1$–$C_6$ alkyl, benzyl, —$(CH_2)_2Si(CH_3)_3$, —$CH_2CH=CH_2$, —$CH_2CHOHCH_2OH$, —$(CH_2)_a$COOH, —$(CH_2)_bNR^{z1}R^{z2}$, —$(CH_2)_cPOR^{z3}R^{z4}$ or —$[(CH_2)_2O]_d$—($C_1$–$C_6$)alkyl;

a, b and c are independently 1, 2, 3, 4, 5 or 6;

$R^{z1}$ and $R^{z2}$ are independently hydrogen, $C_1-C_6$ alkyl, or $R^{z1}$ and $R^{z2}$ combine to form —$CH_2(CH_2)_eCH_2$—;

$R^{z3}$ and $R^{z4}$ are independently hydroxy, or $C_1-C_6$ alkoxy;

d is 1 or 2;

e is 1, 2 or 3;

$R^{x2}$, $R^{y1}$, $R^{y2}$, $R^{y3}$ and $R^{y4}$ are independently hydroxy or hydrogen;

$R_0$ is hydroxy, —OP(O)(OH)$_2$ or a group of the formulae:

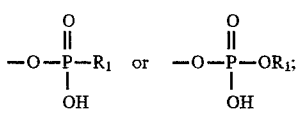

$R_1$ is $C_1-C_6$ alkyl, phenyl, p-halo-phenyl, p-nitrophenyl, benzyl, p-halo-benzyl or p-nitro-benzyl;

I) $R_2$ is a group of the formula

where:

A) $R_3$ is $C_1-C_{12}$ alkyl, $C_1-C_6$ alkoxy or quinolyl;

B) $R_3$ is —O—$(CH_2)_m$—[O—$(CH_2)_n]_p$—O—$(C_1-C_{12}$ alkyl);

m and n are independently 2, 3 or 4;

p is 0 or 1; or

C) $R_3$ is —Y—$(C_1-C_{12}$ alkyl);

Y is —C≡C— or —CH=CH—; or

D) $R_3$ is —O—$(CH_2)_q$—G;

q is 2, 3 or 4;

G is $C_7-C_{10}$ bicycloalkyl or $C_7-C_{14}$ tricycloalkyl; or

II) $R_2$ is a group of the formula

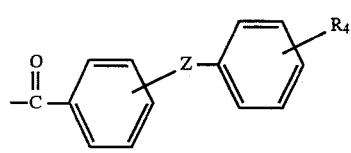

where:

Z is —O—, —C≡C—, —CH=CH—, —$CH_2$—$CH_2$—, —$CH_2$—, or a bond;

A) $R_4$ is hydrogen, $C_1-C_{12}$ alkyl, $C_1-C_{12}$ substituted alkyl, $C_2-C_{12}$ alkenyl, $C_2-C_{12}$ substituted alkenyl, $C_2-C_{12}$ alkynyl, $C_2-C_{12}$ substituted alkynyl, $C_1-C_{12}$ alkoxy, $C_3-C_{12}$ cycloalkyl, $C_7-C_{10}$ bicycloalkyl, $C_7-C_{14}$ tricycloalkyl, $C_3-C_{12}$ cycloalkoxy, naphthyl, pyridyl, thienyl, benzothienyl, quinolyl or phenyl; or B) $R_4$ is phenyl substituted by amino, $C_1-C_{12}$ alkylthio, halo, $C_1-C_{12}$ alkyl, $C_2-C_{12}$ alkenyl, $C_2-C_{12}$ alkynyl, $C_1-C_{12}$ substituted alkyl, $C_2-C_{12}$ substituted alkenyl, $C_2-C_{12}$ substituted alkynyl, $C_1-C_{12}$ alkoxy, trifluoromethyl, phenyl, substituted phenyl, or phenyl substituted with a group of the formula —O—$(CH_2)_m$—[O—$(CH_2)_n]_p$—O—$(C_1-C_{12}$ alkyl) where m, n and p are as defined above; or C) $R_4$ is $C_1-C_{12}$ alkoxy substituted with halo, $C_3-C_{12}$ cycloalkyl, $C_7-C_{10}$ bicycloalkyl, $C_7-C_{14}$ tricycloalkyl, $C_1-C_6$ alkoxy, $C_2-C_{12}$ alkynyl, amino, $C_1-C_4$ alkylamino, di($C_1-C_4$ alkyl)amino, formamido, $C_2-C_{12}$ alkanoylamino, or phenyl substituted with a group of the formula —O—$(CH_2)_m$—[O—$(CH_2)_n]_p$—O—$(C_1-C_{12}$ alkyl) where m, n and p are as defined above; or D) $R_4$ is —O—$(CH_2)_r$—W—$R_5$;

r is 2, 3 or 4;

W is pyrrolidino, piperidino or piperazino;

$R_5$ is hydrogen, $C_1-C_{12}$ alkyl, $C_3-C_{12}$ cycloalkyl, benzyl or $C_3-C_{12}$ cycloalkylmethyl; or E) $R_4$ is —$Y^1$—$R_6$;

$Y^1$ is —C≡C— or —CH=CH—;

$R_6$ is $C_3-C_{12}$ cycloalkyl, $C_7-C_{10}$ bicycloalkyl, $C_7-C_{14}$ tricycloalkyl, $C_3-C_{12}$ cycloalkenyl, naphthyl, benzothiazolyl, thienyl, indanyl, fluorenyl, or phenyl substituted with $C_1-C_{12}$ alkylthio, $C_2-C_{12}$ alkenyl, $C_2-C_{12}$ alkynyl, halo($C_1-C_6$ alkoxy) or a group of the formula —O—$(CH_2)_r$—W—$R_5$ where r, W and $R_5$ are as defined above; or $R_6$ is phenyl substituted with a group of the formula —O—$(CH_2)_m$—[O—$(CH_2)_n]_p$—O—$(C_1-C_{12}$ alkyl) where m, n and p are as defined above; or F) $R_4$ is $C_1-C_{12}$ alkoxy substituted with a group of the formula —NHC(O)$R_7$;

$R_7$ is $C_1-C_6$ alkoxy, or phenyl($C_1-C_6$ alkoxy); or

III) $R_2$ is a group of the formula

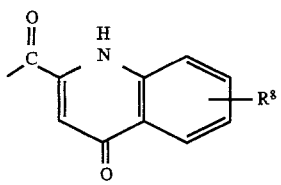

where $R^8$ is $C_1-C_{12}$ alkoxy or a group of the formula —O—$(CH_2)_m$—[O—$(CH_2)_n]_p$—O—$(C_1-C_{12}$ alkyl) where m, n and p are as defined above; or IV) $R_2$ is a group of the formula

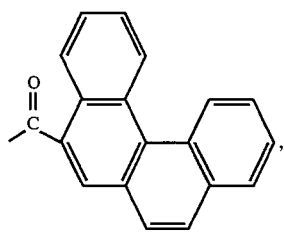

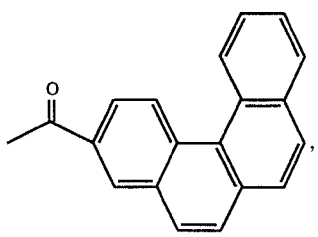

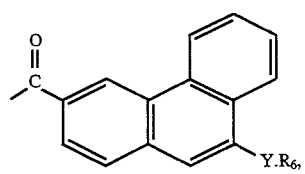

-continued

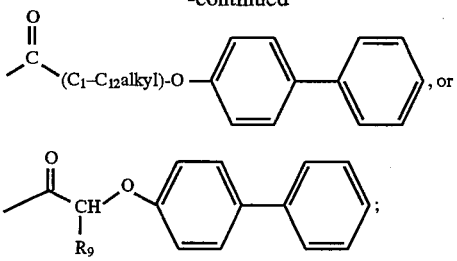

where:

Y and $R_6$ are as defined above;

$R_9$ is phenyl, $C_1$–$C_{12}$ alkyl, or $C_1$–$C_{12}$ alkoxy; or

V) $R_2$ is naphthoyl substituted with $R_4$ where $R_4$ is as defined above;

i) when R' is —$CH_2C(O)NH_2$; and $R^{x1}$ is methyl or benzyl; then $R_2$ is not a group of the formula

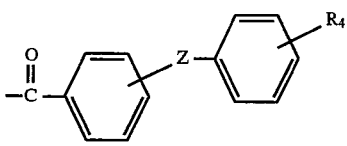

where:
Z is a bond;
A) $R_4$ is $C_1$–$C_{12}$ alkoxy; or
B) $R_4$ is phenyl substituted by $C_1$–$C_{12}$ alkoxy; or
C) $R_4$ is $C_1$–$C_{12}$ alkoxy substituted with $C_1$–$C_4$ alkylamino, di($C_1$–$C_4$ alkyl) amino; or
D) $R_4$ is —O—$(CH_2)_r$—W—$R_5$;
W is piperidino or piperazino;

ii) when $R^{x1}$ is —$(CH_2)_b NR^{z1}R^{z2}$; then $R_2$ is not a group of the formula

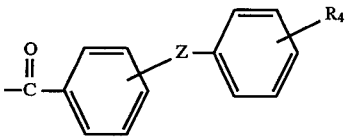

where:
Z is a bond;
A) $R_4$ is $C_1$–$C_{12}$ alkoxy; or
B) $R_4$ is phenyl substituted by $C_1$–$C_{12}$ alkoxy; or
C) $R_4$ is $C_1$–$C_{12}$ alkoxy substituted with $C_1$–$C_4$ alkylamino, di($C_1$–$C_4$ alkyl)amino; or
D) $R_4$ is —O—$(CH_2)_r$—W—$R_5$;
W is piperidino or piperazino;

or a pharmaceutically acceptable salt thereof.

2. A compound according to claim 1 where:
R', R" and R'" are each methyl;
$R^{y1}$, $R^{y2}$, $R^{y3}$ and $R^{y4}$ are each hydroxy;
$R^{x2}$ is hydroxy;
$R_0$ is hydroxy or a group of the formulae:

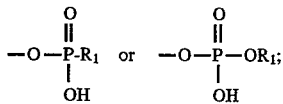

$R_1$ is methyl;
or a pharmaceutically acceptable salt thereof.

3. A compound according to claim 2 where $R_2$ is a group of the formula:

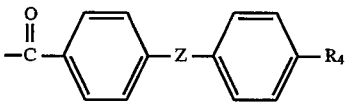

where

Z is —C≡C— or a bond;

A) $R_4$ is hydrogen, $C_1$–$C_{12}$ alkyl, $C_1$–$C_{12}$ substituted alkyl, $C_2$–$C_{12}$ alkenyl, $C_2$–$C_{12}$ substituted alkenyl, $C_2$–$C_{12}$ alkynyl, $C_2$–$C_{12}$ substituted alkynyl, $C_1$–$C_{12}$ alkoxy, $C_3$–$C_{12}$ cycloalkyl, $C_7$–$C_{10}$ bicycloalkyl, $C_7$–$C_{14}$ tricycloalkyl, $C_3$–$C_{12}$ cycloalkoxy, naphthyl, pyridyl, thienyl, benzothienyl, quinolyl or phenyl; or B) $R_4$ is phenyl substituted by amino, $C_1$–$C_{12}$ alkylthio, halo, $C_1$–$C_{12}$ alkyl, $C_2$–$C_{12}$ alkenyl, $C_2$–$C_{12}$ alkynyl, $C_1$–$C_{12}$ substituted alkyl, $C_2$–$C_{12}$ substituted alkenyl, $C_2$–$C_{12}$ substituted alkynyl, $C_1$–$C_{12}$ alkoxy, trifluoromethyl, phenyl, substituted phenyl, or a group of the formula —O—$(CH_2)_m$—[O—$(CH_2)_n]_p$—O—($C_1$–$C_{12}$ alkyl) where m, n and p are as defined above; or C) $R_4$ is $C_1$–$C_{12}$ alkoxy substituted with halo, $C_3$–$C_{12}$ cycloalkyl, $C_7$–$C_{10}$ bicycloalkyl, $C_7$–$C_{14}$ tricycloalkyl, $C_1$–$C_6$ alkoxy, $C_2$–$C_{12}$ alkynyl, amino, $C_1$–$C_4$ alkylamino, di($C_1$–$C_4$ alkyl)amino, formamido, $C_2$–$C_{12}$ alkanoylamino, or phenyl substituted with a group of the formula —O—$(CH_2)_m$—[O—$(CH_2)_n]_p$—O—($C_1$–$C_{12}$ alkyl) where m, n and p are as defined above; or D) $R_4$ is —O—$(CH_2)_r$—W—$R_5$;
r is 2, 3 or 4;
W is pyrrolidino, piperidino or piperazino;
$R_5$ is hydrogen, $C_1$–$C_{12}$ alkyl, $C_3$–$C_{12}$ cycloalkyl, benzyl or $C_3$–$C_{12}$ cycloalkylmethyl; or E) $R_4$ is —$Y^1$—$R_6$;
$Y^1$ is —C≡C— or —CH=CH—;
$R_6$ is $C_3$–$C_{12}$ cycloalkyl, $C_7$–$C_{10}$ bicycloalkyl, $C_7$–$C_{14}$ tricycloalkyl, $C_3$–$C_{12}$ cycloalkenyl, naphthyl, benzothiazolyl, thienyl, indanyl, fluorenyl, or phenyl substituted with $C_1$–$C_{12}$ alkylthio, $C_2$–$C_{12}$ alkenyl, $C_2$–$C_{12}$ alkynyl, halo($C_1$–$C_6$ alkoxy) or a group of the formula —O—$(CH_2)_r$—W—$R_5$ where r, W and $R_5$ are as defined above; or $R_6$ is phenyl substituted with a group of the formula —O—$(CH_2)_m$—[O—$(CH_2)_n]_p$—O—($C_1$–$C_{12}$ alkyl) where m, n and p are as defined above; or F) $R_4$ is $C_1$–$C_{12}$ alkoxy substituted with a group of the formula —NHC(O)$R_7$;
$R_7$ is $C_1$–$C_6$ alkoxy, or phenyl($C_1$–$C_6$ alkoxy);

or a pharmaceutically acceptable salt thereof.

4. A compound according to claim 3 where:

A) $R_4$ is $C_2$–$C_{12}$ alkynyl, $C_2$–$C_{12}$ substituted alkynyl, $C_1$–$C_{12}$ alkoxy, $C_3$–$C_{12}$ cycloalkoxy, or phenyl; or B) $R_4$ is phenyl substituted by $C_1$–$C_{12}$ alkoxy, or a group of the formula —O—$(CH_2)_2$—O—($C_1$–$C_6$ alkyl); or C) $R_4$ is $C_1$–$C_{12}$ alkoxy substituted with $C_3$–$C_{12}$ cycloalkyl; or D) $R_4$ is —O—$(CH_2)_r$—W—$R_5$;
r is 2 or 3;
W is piperidino;
$R_5$ is hydrogen, $C_1$–$C_{12}$ alkyl, $C_3$–$C_{12}$ cycloalkyl, benzyl or $C_3$–$C_{12}$ cycloalkylmethyl; or E) $R_4$ is $-Y^1-R_6$;
   $Y^1$ is $-C\equiv C-$;
   $R_6$ is phenyl substituted with $C_1-C_{12}$ alkylthio, $C_2-C_{12}$ alkenyl, $C_2-C_{12}$ alkynyl, halo($C_1-C_6$ alkoxy);
   or $R_6$ is phenyl substituted with a group of the formula $-O-(CH_2)_r-W-R_5$ where r, W and $R_5$ are as defined above;
   or $R_6$ is phenyl substituted with a group of the formula $-O-(CH_2)_2-O-(C_1-C_6$ alkyl);
or a pharmaceutically acceptable salt thereof.

5. A compound according to claim 4 where:
   $R_4$ is $C_2-C_{12}$ alkynyl, $C_2-C_{12}$ substituted alkynyl, $C_1-C_{12}$ alkoxy, or phenyl; or
   $R_4$ is phenyl substituted by $C_1-C_{12}$ alkoxy, or a group of the formula $-O-(CH_2)_2-O-(C_1-C_6$ alkyl); or
   $R_4$ is $-Y^1-R_6$;
   $Y^1$ is $-C\equiv C-$;
   $R_6$ is phenyl substituted with a group of the formula $-O-(CH_2)_2-O-(C_1-C_6$ alkyl);
or a pharmaceutically acceptable salt thereof.

6. A compound according to claim 5 where:
   $R^{x1}$ is $C_1-C_4$ alkyl, benzyl, $-CH_2CHOHCH_2OH$, $-CH_2COOH$, $-(CH_2)_bNR^{z1}R^{z2}$ or $-(CH_2)_2POR^{z3}R^{z4}$;
   b is 2, 3, 4, 5 or 6;
   $R^{z1}$ and $R^{z2}$ are independently hydrogen or $C_1-C_4$ alkyl; and
   $R^{z3}$ and $R^{z4}$ are independently hydrogen or methoxy;
or a pharmaceutically acceptable salt thereof.

7. A compound according to claim 6 where:
   $R^{x1}$ is methyl, benzyl, $-CH_2CHOHCH_2OH$, $-CH_2COOH$, $-(CH_2)_2NR^{z1}R^{z2}$ or $-(CH_2)_2POR^{z3}R^{z4}$;
   $R^{z1}$ and $R^{z2}$ are independently hydrogen or methyl; and
   $R^{z3}$ and $R^{z4}$ are independently hydrogen or methoxy;
or a pharmaceutically acceptable salt thereof.

8. A compound according to claim 7 where:
   $R^{x1}$ is $-CH_2CHOHCH_2OH$, $-CH_2COOH$ or $-(CH_2)_2POR^{z3}R^{z4}$; and
   $R^{z3}$ and $R^{z4}$ are independently hydrogen or methoxy;
or a pharmaceutically acceptable salt thereof.

9. The compound according to claim 8 where:
   $R_0$ is hydroxy;

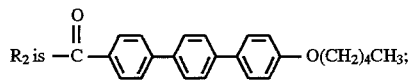

and
   $R^{x1}$ is $-CH_2CHOHCH_2OH$;
or a pharmaceutically acceptable salt thereof.

10. The compound according to claim 7 where:
    $R_0$ is hydroxy;

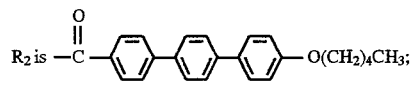

and
    $R^{x1}$ is methyl;
or a pharmaceutically acceptable salt thereof.

11. A pharmaceutical formulation comprising one or more pharmaceutically acceptable carriers, diluents or excipients and a compound of claim 1.

12. A pharmaceutical formulation according to claim 11 where the compound is one where:
    R', R" and R'" are each methyl;
    $R^{y1}$, $R^{y2}$, $R^{y3}$ and $R^{y4}$ are each hydroxy;
    $R^{x2}$ is hydroxy;
    $R_0$ is hydroxy or a group of the formulae:

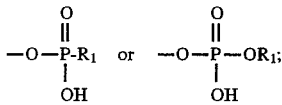

$R_1$ is methyl;
or a pharmaceutically acceptable salt thereof.

13. A pharmaceutical formulation according to claim 12 where the compound is one where:

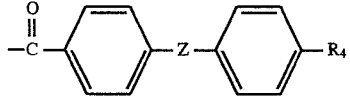

where
    Z is $-C\equiv C-$ or a bond;
    A) $R_4$ is hydrogen, $C_1-C_{12}$ alkyl, $C_1-C_{12}$ substituted alkyl, $C_2-C_{12}$ alkenyl, $C_2-C_{12}$ substituted alkenyl, $C_2-C_{12}$ alkynyl, $C_2-C_{12}$ substituted alkynyl, $C_1-C_{12}$ alkoxy, $C_3-C_{12}$ cycloalkyl, $C_7-C_{10}$ bicycloalkyl, $C_7-C_{14}$ tricycloalkyl, $C_3-C_{12}$ cycloalkoxy, naphthyl, pyridyl, thienyl, benzothienyl, quinolyl or phenyl; or
    B) $R_4$ is phenyl substituted by amino, $C_1-C_{12}$ alkylthio, halo, $C_1-C_{12}$ alkyl, $C_2-C_{12}$ alkenyl, $C_2-C_{12}$ alkynyl, $C_1-C_{12}$ substituted alkyl, $C_2-C_{12}$ substituted alkenyl, $C_2-C_{12}$ substituted alkynyl, $C_1-C_{12}$ alkoxy, trifluoromethyl, phenyl, substituted phenyl, or a group of the formula $-O-(CH_2)_m-[O-(CH_2)_n]_p-O-(C_1-C_{12}$ alkyl) where m, n and p are as defined above; or
    C) $R_4$ is $C_1-C_{12}$ alkoxy substituted with halo, $C_3-C_{12}$ cycloalkyl, $C_7-C_{10}$ bicycloalkyl, $C_7-C_{14}$ tricycloalkyl, $C_1-C_6$ alkoxy, $C_2-C_{12}$ alkynyl, amino, $C_1-C_4$ alkylamino, di($C_1-C_4$ alkyl)amino, formamido, $C_2-C_{12}$ alkanoylamino, or phenyl substituted with a group of the formula $-O-(CH_2)_m-[O-(CH_2)_n]_p-O-(C_1-C_{12}$ alkyl) where m, n and p are as defined above; or
    D) $R_4$ is $-O-(CH_2)_r-W-R_5$;
       r is 2, 3 or 4;
       W is pyrrolidino, piperidino or piperazino;
       $R_5$ is hydrogen, $C_1-C_{12}$ alkyl, $C_3-C_{12}$ cycloalkyl, benzyl or $C_3-C_{12}$ cycloalkylmethyl; or
    E) $R_4$ is $-Y^1-R_6$;
       $Y^1$ is $-C\equiv C-$ or $-CH=CH-$;
       $R_6$ is $C_3-C_{12}$ cycloalkyl, $C_7-C_{10}$ bicycloalkyl, $C_7-C_{14}$ tricycloalkyl, $C_3-C_{12}$ cycloalkenyl, naphthyl, benzothiazolyl, thienyl, indanyl, fluorenyl, or phenyl substituted with $C_1-C_{12}$ alkylthio, $C_2-C_{12}$ alkenyl, $C_2-C_{12}$ alkynyl, halo($C_1-C_6$ alkoxy) or a group of the formula $-O-(CH_2)_r-W-R_5$ where r, W and $R_5$ are as defined above; or
       $R_6$ is phenyl substituted with a group of the formula $-O-(CH_2)_m-[O-(CH_2)_n]_p-O-(C_1-C_{12}$ alkyl) where m, n and p are as defined above; or
    F) $R_4$ is $C_1-C_{12}$ alkoxy substituted with a group of the formula $-NHC(O)R_7$;

$R_7$ is $C_1$–$C_6$ alkoxy, or phenyl($C_1$–$C_6$ alkoxy);
or a pharmaceutically acceptable salt thereof.

14. A pharmaceutical formulation according to claim 13 where the compound is one where:

A) $R_4$ is $C_2$–$C_{12}$ alkynyl, $C_2$–$C_{12}$ substituted alkynyl, $C_1$–$C_{12}$ alkoxy, $C_3$–$C_{12}$ cycloalkoxy, or phenyl; or B) $R_4$ is phenyl substituted by $C_1$–$C_{12}$ alkoxy, or a group of the formula —O—$(CH_2)_2$—O—($C_1$–$C_6$ alkyl); or C) $R_4$ is $C_1$–$C_{12}$ alkoxy substituted with $C_3$–$C_{12}$ cycloalkyl; or D) $R_4$ is —O—$(CH_2)_r$—W—$R_5$;
r is 2 or 3;
W is piperidino;
$R_5$ is hydrogen, $C_1$–$C_{12}$ alkyl, $C_3$–$C_{12}$ cycloalkyl, benzyl or $C_3$–$C_{12}$ cycloalkylmethyl; or E) $R_4$ is —$Y^1$—$R_6$;
$Y^1$ is —C≡C—;
$R_6$ is phenyl substituted with $C_1$–$C_{12}$ alkylthio, $C_2$–$C_{12}$ alkenyl, $C_2$–$C_{12}$ alkynyl, halo($C_1$–$C_6$ alkoxy);
or $R_6$ is phenyl substituted with a group of the formula —O—$(CH_2)_r$—W—$R_5$ where r, W and $R_5$ are as defined above;
or $R_6$ is phenyl substituted with a group of the formula —O—$(CH_2)_2$—O—($C_1$–$C_6$ alkyl);
or a pharmaceutically acceptable salt thereof.

15. A pharmaceutical formulation according to claim 14 where the compound is one where:

$R_4$ is $C_2$–$C_{12}$ alkynyl, $C_2$–$C_{12}$ substituted alkynyl, $C_1$–$C_{12}$ alkoxy, or phenyl; or $R_4$ is phenyl substituted by $C_1$–$C_{12}$ alkoxy, or a group of the formula —O—$(CH_2)_2$—O—($C_1$–$C_6$ alkyl); or $R_4$ is —$Y^1$—$R_6$;
$Y^1$ is —C≡C—;
$R_6$ is phenyl substituted with a group of the formula —O—$(CH_2)_2$—O—($C_1$–$C_6$ alkyl);
or a pharmaceutically acceptable salt thereof.

16. A pharmaceutical formulation according to claim 15 where the compound is one where:

$R^{x1}$ is $C_1$–$C_4$ alkyl, benzyl, —$CH_2CHOHCH_2OH$, —$CH_2COOH$, —$(CH_2)_bNR^{z1}R^{z2}$ or —$(CH_2)_2POR^{z3}R^{z4}$;
b is 2, 3, 4, 5 or 6;
$R^{z1}$ and $R^{z2}$ are independently hydrogen or $C_1$–$C_4$ alkyl; and
$R^{z3}$ and $R^{z4}$ are independently hydrogen or methoxy;
or a pharmaceutically acceptable salt thereof.

17. A pharmaceutical formulation according to claim 16 where the compound is one where:

$R^{x1}$ is methyl, benzyl, —$CH_2CHOHCH_2OH$, —$CH_2COOH$, —$(CH_2)_2NR^{z1}R^{z2}$ or —$(CH_2)_2POR^{z3}R^{z4}$;
$R^{z1}$ and $R^{z2}$ are independently hydrogen or methyl; and
$R^{z3}$ and $R^{z4}$ are independently hydrogen or methoxy;
or a pharmaceutically acceptable salt thereof.

18. A pharmaceutical formulation according to claim 17 where the compound is one where:

$R^{x1}$ is —$CH_2CHOHCH_2OH$, —$CH_2COOH$ or —$(CH_2)_2POR^{z3}R^{z4}$; and
$R^{z3}$ and $R^{z4}$ are independently hydrogen or methoxy;
or a pharmaceutically acceptable salt thereof.

19. The pharmaceutical formulation according to claim 18 where the compound is one where:

$R_0$ is hydroxy;

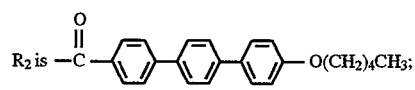

and $R^{x1}$ is —$CH_2CHOHCH_2OH$;
or a pharmaceutically acceptable salt thereof.

20. The pharmaceutical formulation according to claim 17 where the compound is one where:

$R_0$ is hydroxy;

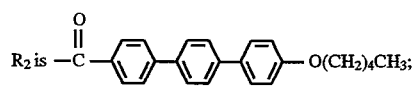

and $R^{x1}$ is methyl;
or a pharmaceutically acceptable salt thereof.

21. A method of inhibiting fungal activity comprising contacting a compound of claim 1 with a fungus.

22. A method according to claim 21 where the compound is one where:

R', R" and R'" are each methyl;
$R^{y1}$, $R^{y2}$, $R^{y3}$ and $R^{y4}$ are each hydroxy;
$R^{x2}$ is hydroxy;
$R_0$ is hydroxy or a group of the formulae:

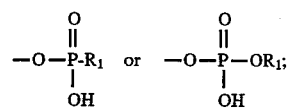

$R_1$ is methyl;
or a pharmaceutically acceptable salt thereof.

23. A method according to claim 22 where the compound is one where:

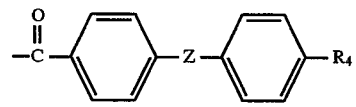

where

Z is —C≡C— or a bond;

A) $R_4$ is hydrogen, $C_1$–$C_{12}$ alkyl, $C_1$–$C_{12}$ substituted alkyl, $C_2$–$C_{12}$ alkenyl, $C_2$–$C_{12}$ substituted alkenyl, $C_2$–$C_{12}$ alkynyl, $C_2$–$C_{12}$ substituted alkynyl, $C_1$–$C_{12}$ alkoxy, $C_3$–$C_{12}$ cycloalkyl, $C_7$–$C_{10}$ bicycloalkyl, $C_7$–$C_{14}$ tricycloalkyl, $C_3$–$C_{12}$ cycloalkoxy, naphthyl, pyridyl, thienyl, benzothienyl, quinolyl or phenyl; or B) $R_4$ is phenyl substituted by amino, $C_1$–$C_{12}$ alkylthio, halo, $C_1$–$C_{12}$ alkyl, $C_2$–$C_{12}$ alkenyl, $C_2$–$C_{12}$ alkynyl, $C_1$–$C_{12}$ substituted alkyl, $C_2$–$C_{12}$ substituted alkenyl, $C_2$–$C_{12}$ substituted alkynyl, $C_1$–$C_{12}$ alkoxy, trifluoromethyl, phenyl, substituted phenyl, or a group of the formula —O—$(CH_2)_m$—[O—$(CH_2)_n]_p$—O—($C_1$–$C_{12}$ alkyl) where m, n and p are as defined above; or C) $R_4$ is $C_1$–$C_{12}$ alkoxy substituted with halo, $C_3$–$C_{12}$ cycloalkyl, $C_7$–$C_{10}$ bicycloalkyl, $C_7$–$C_{14}$ tricycloalkyl, $C_1$–$C_6$ alkoxy, $C_2$–$C_{12}$ alkynyl, amino, $C_1$–$C_4$ alkylamino, di($C_1$–$C_4$ alkyl)amino, formamido, $C_2-C_{12}$ alkanoylamino, or phenyl substituted with a group of the formula —O—$(CH_2)_m$—[O—$(CH_2)_n]_p$—O—($C_1-C_{12}$ alkyl) where m, n and p are as defined above; or D) $R_4$ is —O—$(CH_2)_r$—W—$R_5$;
r is 2, 3 or 4;
W is pyrrolidino, piperidino or piperazino;
$R_5$ is hydrogen, $C_1-C_{12}$ alkyl, $C_3-C_{12}$ cycloalkyl, benzyl or $C_3-C_{12}$ cycloalkylmethyl; or E) $R_4$ is —$Y^1$—$R_6$;
$Y^1$ is —C≡C— or —CH=CH—;
$R_6$ is $C_3-C_{12}$ cycloalkyl, $C_7-C_{10}$ bicycloalkyl, $C_7-C_{14}$ tricycloalkyl, $C_3-C_{12}$ cycloalkenyl, naphthyl, benzothiazolyl, thienyl, indanyl, fluorenyl, or phenyl substituted with $C_1-C_{12}$ alkylthio, $C_2-C_{12}$ alkenyl, $C_2-C_{12}$ alkynyl, halo($C_1-C_6$ alkoxy) or a group of the formula —O—$(CH_2)_r$—W—$R_5$ where r, W and $R_5$ are as defined above; or
$R_6$ is phenyl substituted with a group of the formula —O—$(CH_2)_m$—[O—$(CH_2)_n]_p$—O—($C_1-C_{12}$ alkyl) where m, n and p are as defined above; or F) $R_4$ is $C_1-C_{12}$ alkoxy substituted with a group of the formula —NHC(O)$R_7$;
$R_7$ is $C_1-C_6$ alkoxy, or phenyl($C_1-C_6$ alkoxy);
or a pharmaceutically acceptable salt thereof.

24. A method according to claim 23 where the compound is one where:
A) $R_4$ is $C_2-C_{12}$ alkynyl, $C_2-C_{12}$ substituted alkynyl, $C_1-C_{12}$ alkoxy, $C_3-C_{12}$ cycloalkoxy, or phenyl; or
B) $R_4$ is phenyl substituted by $C_1-C_{12}$ alkoxy, or a group of the formula —O—$(CH_2)_2$—O—($C_1-C_6$ alkyl); or
C) $R_4$ is $C_1-C_{12}$ alkoxy substituted with $C_3-C_{12}$ cycloalkyl; or
D) $R_4$ is —O—$(CH_2)_r$—W—$R_5$;
r is 2 or 3;
W is piperidino;
$R_5$ is hydrogen, $C_1-C_{12}$ alkyl, $C_3-C_{12}$ cycloalkyl, benzyl or $C_3-C_{12}$ cycloalkylmethyl; or
E) $R_4$ is —$Y^1$—$R_6$;
$Y^1$ is —C≡C—;
$R_6$ is phenyl substituted with $C_1-C_{12}$ alkylthio, $C_2-C_{12}$ alkenyl, $C_2-C_{12}$ alkynyl, halo($C_1-C_6$ alkoxy);
or $R_6$ is phenyl substituted with a group of the formula —O—$(CH_2)_r$—W—$R_5$ where r, W and $R_5$ are as defined above;
or $R_6$ is phenyl substituted with a group of the formula —O—$(CH_2)_2$—O—($C_1-C_6$ alkyl);
or a pharmaceutically acceptable salt thereof.

25. A method according to claim 24 where the compound is one where:
$R_4$ is $C_2-C_{12}$ alkynyl, $C_2-C_{12}$ substituted alkynyl, $C_1-C_{12}$ alkoxy, or phenyl; or
$R_4$ is phenyl substituted by $C_1-C_{12}$ alkoxy, or a group of the formula —O—$(CH_2)_2$—O—($C_1-C_6$ alkyl); or
$R_4$ is —$Y^1$—$R_6$;
$Y^1$ is —C≡C—;
$R_6$ is phenyl substituted with a group of the formula —O—$(CH_2)_2$—O—($C_1-C_6$ alkyl);
or a pharmaceutically acceptable salt thereof.

26. A method according to claim 25 where the compound is one where:
$R^{x1}$ is $C_1-C_4$ alkyl, benzyl, —$CH_2CHOHCH_2OH$, —$CH_2COOH$, —$(CH_2)_b NR^{z1}R^{z2}$ or —$(CH_2)_2 POR^{z3}R^{z4}$;
b is 2, 3, 4, 5 or 6;

$R^{z1}$ and $R^{z2}$ are independently hydrogen or $C_1-C_4$ alkyl; and $R^{z3}$ and $R^{z4}$ are independently hydrogen or methoxy;
or a pharmaceutically acceptable salt thereof.

27. A method according to claim 26 where the compound is one where:
$R^{x1}$ is methyl, benzyl, —$CH_2CHOHCH_2OH$, —$CH_2COOH$, —$(CH_2)_2 NR^{z1}R^{z2}$ or —$(CH_2)_2 POR^{z3}R^{z4}$;

$R^{z1}$ and $R^{z2}$ are independently hydrogen or methyl; and $R^{z3}$ and $R^{z4}$ are independently hydrogen or methoxy;
or a pharmaceutically acceptable salt thereof.

28. A method according to claim 27 where the compound is one where:
$R^{x1}$ is —$CH_2CHOHCH_2OH$, —$CH_2COOH$ or —$(CH_2)_2 POR^{z3}R^{z4}$; and $R^{z3}$ and $R^{z4}$ are independently hydrogen or methoxy;
or a pharmaceutically acceptable salt thereof.

29. The method according to claim 28 where the compound is one where:
$R_0$ is hydroxy;

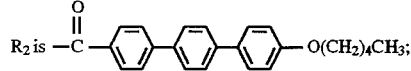

and
$R^{x1}$ is —$CH_2CHOHCH_2OH$;
or a pharmaceutically acceptable salt thereof.

30. The method according to claim 27 where the compound is one where:
$R_0$ is hydroxy;

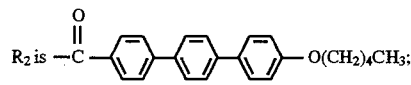

and
$R^{x1}$ is methyl;
or a pharmaceutically acceptable salt thereof.

31. A method according to claim 26 where the fungus is *Candida albicans.*

32. A method according to claim 26 where the fungus is *Aspergillus fumigatus.*

33. A method of treating a fungal infection which comprises administering an effective amount of a compound of claim 1 to a host in need of such treatment.

34. A method according to claim 33 where the compound is one where:
R', R" and R'" are each methyl;
$R^{y1}$, $R^{y2}$, $R^{y3}$ and $R^{y4}$ are each hydroxy;
$R^{x2}$ is hydroxy;
$R_0$ is hydroxy or a group of the formulae:

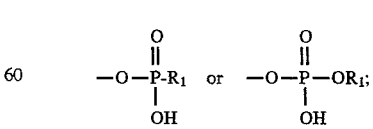

$R_1$ is methyl;
or a pharmaceutically acceptable salt thereof.

35. A method according to claim 34 where the compound is one where:

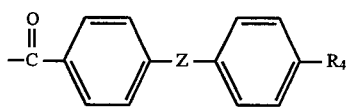

where

Z is —C≡C— or a bond;

A) $R_4$ is hydrogen, $C_1$–$C_{12}$ alkyl, $C_1$–$C_{12}$ substituted alkyl, $C_2$–$C_{12}$ alkenyl, $C_2$–$C_{12}$ substituted alkenyl, $C_2$–$C_{12}$ alkynyl, $C_2$–$C_{12}$ substituted alkynyl, $C_1$–$C_{12}$ alkoxy, $C_3$–$C_{12}$ cycloalkyl, $C_7$–$C_{10}$ bicycloalkyl, $C_7$–$C_{14}$ tricycloalkyl, $C_3$–$C_{12}$ cycloalkoxy, naphthyl, pyridyl, thienyl, benzothienyl, quinolyl or phenyl; or B) $R_4$ is phenyl substituted by amino, $C_1$–$C_{12}$ alkylthio, halo, $C_1$–$C_{12}$ alkyl, $C_2$–$C_{12}$ alkenyl, $C_2$–$C_{12}$ alkynyl, $C_1$–$C_{12}$ substituted alkyl, $C_2$–$C_{12}$ substituted alkenyl, $C_2$–$C_{12}$ substituted alkynyl, $C_1$–$C_{12}$ alkoxy, trifluoromethyl, phenyl, substituted phenyl, or a group of the formula —O—$(CH_2)_m$—[O—$(CH_2)_n]_p$—O—($C_1$–$C_{12}$ alkyl) where m, n and p are as defined above; or C) $R_4$ is $C_1$–$C_{12}$ alkoxy substituted with halo, $C_3$–$C_{12}$ cycloalkyl, $C_7$–$C_{10}$ bicycloalkyl, $C_7$–$C_{14}$ tricycloalkyl, $C_1$–$C_6$ alkoxy, $C_2$–$C_{12}$ alkynyl, amino, $C_1$–$C_4$ alkylamino, di($C_1$–$C_4$ alkyl)amino, formamido, $C_2$–$C_{12}$ alkanoylamino, or phenyl substituted with a group of the formula —O—$(CH_2)_m$—[O—$(CH_2)_n]_p$—O—($C_1$–$C_{12}$ alkyl) where m, n and p are as defined above; or D) $R_4$ is —O—$(CH_2)_r$—W—$R_5$;
r is 2, 3 or 4;
W is pyrrolidino, piperidino or piperazino;
$R_5$ is hydrogen, $C_1$–$C_{12}$ alkyl, $C_3$–$C_{12}$ cycloalkyl, benzyl or $C_3$–$C_{12}$ cycloalkylmethyl; or E) $R_4$ is —$Y^1$—$R_6$;
$Y^1$ is —C≡C— or —CH=CH—;
$R_6$ is $C_3$–$C_{12}$ cycloalkyl, $C_7$–$C_{10}$ bicycloalkyl, $C_7$–$C_{14}$ tricycloalkyl, $C_3$–$C_{12}$ cycloalkenyl, naphthyl, benzothiazolyl, thienyl, indanyl, fluorenyl, or phenyl substituted with $C_1$–$C_{12}$ alkylthio, $C_2$–$C_{12}$ alkenyl, $C_2$–$C_{12}$ alkynyl, halo($C_1$–$C_6$ alkoxy) or a group of the formula —O—$(CH_2)_r$—W—$R_5$ where r, W and $R_5$ are as defined above; or
$R_6$ is phenyl substituted with a group of the formula —O—$(CH_2)_m$—[O—$(CH_2)_n]_p$—O—($C_1$–$C_{12}$ alkyl) where m, n and p are as defined above; or F) $R_4$ is $C_1$–$C_{12}$ alkoxy substituted with a group of the formula —NHC(O)$R_7$;
$R_7$ is $C_1$–$C_6$ alkoxy, or phenyl($C_1$–$C_6$ alkoxy);

or a pharmaceutically acceptable salt thereof.

36. A method according to claim 35 where the compound is one where:

A) $R_4$ is $C_2$–$C_{12}$ alkynyl, $C_2$–$C_{12}$ substituted alkynyl, $C_1$–$C_{12}$ alkoxy, $C_3$–$C_{12}$ cycloalkoxy, or phenyl; or B) $R_4$ is phenyl substituted by $C_1$–$C_{12}$ alkoxy, or a group of the formula —O—$(CH_2)_2$—O—($C_1$–$C_6$ alkyl); or C) $R_4$ is $C_1$–$C_{12}$ alkoxy substituted with $C_3$–$C_{12}$ cycloalkyl; or D) $R_4$ is —O—$(CH_2)_r$—W—$R_5$;
r is 2 or 3;
W is piperidino;
$R_5$ is hydrogen, $C_1$–$C_{12}$ alkyl, $C_3$–$C_{12}$ cycloalkyl, benzyl or $C_3$–$C_{12}$ cycloalkylmethyl; or E) $R_4$ is —$Y^1$—$R_6$;
$Y^1$ is —C≡C—;
$R_6$ is phenyl substituted with $C_1$–$C_{12}$ alkylthio, $C_2$–$C_{12}$ alkenyl, $C_2$–$C_{12}$ alkynyl, halo($C_1$–$C_6$ alkoxy);
or $R_6$ is phenyl substituted with a group of the formula —O—$(CH_2)_r$—W—$R_5$ where r, W and $R_5$ are as defined above;
or $R_6$ is phenyl substituted with a group of the formula —O—$(CH_2)_2$—O—($C_1$–$C_6$ alkyl);

or a pharmaceutically acceptable salt thereof.

37. A method according to claim 36 where the compound is one where:

$R_4$ is $C_2$–$C_{12}$ alkynyl, $C_2$–$C_{12}$ substituted alkynyl, $C_1$–$C_{12}$ alkoxy, or phenyl; or $R_4$ is phenyl substituted by $C_1$–$C_{12}$ alkoxy, or a group of the formula —O—$(CH_2)_2$—O—($C_1$–$C_6$ alkyl); or $R_4$ is —$Y^1$—$R_6$;
$Y^1$ is —C≡C—;
$R_6$ is phenyl substituted with a group of the formula —O—$(CH_2)_2$—O—($C_1$–$C_6$ alkyl);

or a pharmaceutically acceptable salt thereof.

38. A method according to claim 37 where the compound is one where:

$R^{*1}$ is $C_1$–$C_4$ alkyl, benzyl, —$CH_2CHOHCH_2OH$, —$CH_2COOH$, —$(CH_2)_b NR^{z1}R^{z2}$ or —$(CH_2)_2 POR^{z3}R^{z4}$;

b is 2, 3, 4, 5 or 6;

$R^{z1}$ and $R^{z2}$ are independently hydrogen or $C_1$–$C_4$ alkyl; and $R^{z3}$ and $R^{z4}$ are independently hydrogen or methoxy; or a pharmaceutically acceptable salt thereof.

39. A method according to claim 38 where the compound is one where:

$R^{*1}$ is methyl, benzyl, —$CH_2CHOHCH_2OH$, —$CH_2COOH$, —$(CH_2)_2 NR^{z1}R^{z2}$ or —$(CH_2)_2 POR^{z3}R^{z4}$;

$R^{z1}$ and $R^{z2}$ are independently hydrogen or methyl; and $R^{z3}$ and $R^{z4}$ are independently hydrogen or methoxy;

or a pharmaceutically acceptable salt thereof.

40. A method according to claim 39 where the compound is one where:

$R^{*1}$ is —$CH_2CHOHCH_2OH$, —$CH_2COOH$ or —$(CH_2)_2 POR^{z3}R^{z4}$; and $R^{z3}$ and $R^{z4}$ are independently hydrogen or methoxy;

or a pharmaceutically acceptable salt thereof.

41. The method according to claim 40 where the compound is one where:

$R_0$ is hydroxy;

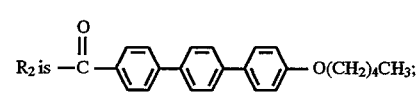

and $R^{*1}$ is —$CH_2CHOHCH_2OH$;

or a pharmaceutically acceptable salt thereof.

42. The method according to claim 39 where the compound is one where:

$R_0$ is hydroxy;

$R_2$ is 
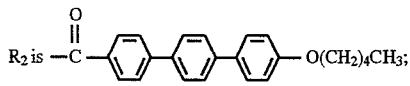
 —C(=O)—⟨phenyl⟩—⟨phenyl⟩—⟨phenyl⟩—O(CH$_2$)$_4$CH$_3$;

and $R^{x1}$ is methyl;

or a pharmaceutically acceptable salt thereof.

43. A method according to claim 38 where the fungal infection is *Candida albicans*.

44. A method according to claim 38 where the fungal infection is *Aspergillus fumigatus*.

45. A method for inhibiting parasitic activity comprising contacting a compound of claim 1 with a parasite.

46. A method according to claim 45 where the compound is one where:

R', R" and R'" are each methyl;
$R^{y1}$, $R^{y2}$, $R^{y3}$ and $R^{y4}$ are each hydroxy;
$R^{x2}$ is hydroxy;
$R_0$ is hydroxy or a group of the formulae:

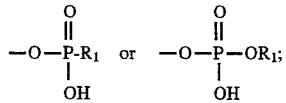

$$-O-\underset{OH}{\overset{O}{\underset{\|}{P}}}-R_1 \quad \text{or} \quad -O-\underset{OH}{\overset{O}{\underset{\|}{P}}}-OR_1;$$

$R_1$ is methyl;
or a pharmaceutically acceptable salt thereof.

47. A method according to claim 46 where the compound is one where:

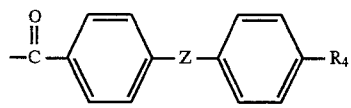

—C(=O)—⟨phenyl⟩—Z—⟨phenyl⟩—R$_4$ where

Z is —C≡C— or a bond;

A) $R_4$ is hydrogen, $C_1$–$C_{12}$ alkyl, $C_1$–$C_{12}$ substituted alkyl, $C_2$–$C_{12}$ alkenyl, $C_2$–$C_{12}$ substituted alkenyl, $C_2$–$C_{12}$ alkynyl, $C_2$–$C_{12}$ substituted alkynyl, $C_1$–$C_{12}$ alkoxy, $C_3$–$C_{12}$ cycloalkyl, $C_7$–$C_{10}$ bicycloalkyl, $C_7$–$C_{14}$ tricycloalkyl, $C_3$–$C_{12}$ cycloalkoxy, naphthyl, pyridyl, thienyl, benzothienyl, quinolyl or phenyl; or B) $R_4$ is phenyl substituted by amino, $C_1$–$C_{12}$ alkylthio, halo, $C_1$–$C_{12}$ alkyl, $C_2$–$C_{12}$ alkenyl, $C_2$–$C_{12}$ alkynyl, $C_1$–$C_{12}$ substituted alkyl, $C_2$–$C_{12}$ substituted alkenyl, $C_2$–$C_{12}$ substituted alkynyl, $C_1$–$C_{12}$ alkoxy, trifluoromethyl, phenyl, substituted phenyl, or a group of the formula —O—(CH$_2$)$_m$—[O—(CH$_2$)$_n$]$_p$—O—(C$_1$–C$_{12}$ alkyl) where m, n and p are as defined above; or C) $R_4$ is $C_1$–$C_{12}$ alkoxy substituted with halo, $C_3$–$C_{12}$ cycloalkyl, $C_7$–$C_{10}$ bicycloalkyl, $C_7$–$C_{14}$ tricycloalkyl, $C_1$–$C_6$ alkoxy, $C_2$–$C_{12}$ alkynyl, amino, $C_1$–$C_4$ alkylamino, di($C_1$–$C_4$ alkyl)amino, formamido, $C_2$–$C_{12}$ alkanoylamino, or phenyl substituted with a group of the formula —O—(CH$_2$)$_m$—[O—(CH$_2$)$_n$]$_p$—O—(C$_1$–C$_{12}$ alkyl) where m, n and p are as defined above; or D) $R_4$ is —O—(CH$_2$)$_r$—W—R$_5$;
r is 2, 3 or 4;
W is pyrrolidino, piperidino or piperazino;
$R_5$ is hydrogen, $C_1$–$C_{12}$ alkyl, $C_3$–$C_{12}$ cycloalkyl, benzyl or $C_3$–$C_{12}$ cycloalkylmethyl; or E) $R_4$ is —Y$^1$—R$_6$;
$Y^1$ is —C≡C— or —CH=CH—;
$R_6$ is $C_3$–$C_{12}$ cycloalkyl, $C_7$–$C_{10}$ bicycloalkyl, $C_7$–$C_{14}$ tricycloalkyl, $C_3$–$C_{12}$ cycloalkenyl, naphthyl, benzothiazolyl, thienyl, indanyl, fluorenyl, or phenyl substituted with $C_1$–$C_{12}$ alkylthio, $C_2$–$C_{12}$ alkenyl, $C_2$–$C_{12}$ alkynyl, halo($C_1$–$C_6$ alkoxy) or a group of the formula —O—(CH$_2$)$_r$—W—R$_5$ where r, W and $R_5$ are as defined above; or $R_6$ is phenyl substituted with a group of the formula —O—(CH$_2$)$_m$—[O—(CH$_2$)$_n$]$_p$—O—(C$_1$–C$_{12}$ alkyl) where m, n and p are as defined above; or F) $R_4$ is $C_1$–$C_{12}$ alkoxy substituted with a group of the formula —NHC(O)R$_7$;
R7 is $C_1$–$C_6$ alkoxy, or phenyl($C_1$–$C_6$ alkoxy);

or a pharmaceutically acceptable salt thereof.

48. A method according to claim 47 where the compound is one where:

A) $R_4$ is $C_2$–$C_{12}$ alkynyl, $C_2$–$C_{12}$ substituted alkynyl, $C_1$–$C_{12}$ alkoxy, $C_3$–$C_{12}$ cycloalkoxy, or phenyl; or B) $R_4$ is phenyl substituted by $C_1$–$C_{12}$ alkoxy, or a group of the formula —O—(CH$_2$)$_2$—O—(C$_1$–C$_6$ alkyl); or C) $R_4$ is $C_1$–$C_{12}$ alkoxy substituted with $C_3$–$C_{12}$ cycloalkyl; or D) $R_4$ is —O—(CH$_2$)$_r$—W—R$_5$;
r is 2 or 3;
W is piperidino;
$R_5$ is hydrogen, $C_1$–$C_{12}$ alkyl, $C_3$–$C_{12}$ cycloalkyl, benzyl or $C_3$–$C_{12}$ cycloalkylmethyl; or E) $R_4$ is —Y$^1$—R$_6$;
$Y^1$ is —C≡C—;
$R_6$ is phenyl substituted with $C_1$–$C_{12}$ alkylthio, $C_2$–$C_{12}$ alkenyl, $C_2$–$C_{12}$ alkynyl, halo($C_1$–$C_6$ alkoxy);
or $R_6$ is phenyl substituted with a group of the formula —O—(CH$_2$)$_r$—W—R$_5$ where r, W and $R_5$ are as defined above;
or $R_6$ is phenyl substituted with a group of the formula —O—(CH$_2$)$_2$—O—(C$_1$–C$_6$ alkyl);

or a pharmaceutically acceptable salt thereof.

49. A method according to claim 48 where the compound is one where:

$R_4$ is $C_2$–$C_{12}$ alkynyl, $C_2$–$C_{12}$ substituted alkynyl, $C_1$–$C_{12}$ alkoxy, or phenyl; or $R_4$ is phenyl substituted by $C_1$–$C_{12}$ alkoxy, or a group of the formula —O—(CH$_2$)$_2$—O—(C$_1$–C$_6$ alkyl); or $R_4$ is —Y$^1$—R$_6$;
$Y^1$ is —C≡C—;
$R_6$ is phenyl substituted with a group of the formula —O—(CH$_2$)$_2$—O—(C$_1$–C$_6$ alkyl);

or a pharmaceutically acceptable salt thereof.

50. A method according to claim 49 where the compound is one where:

$R^{x1}$ is $C_1$–$C_4$ alkyl, benzyl, —CH$_2$CHOHCH$_2$OH, —CH$_2$COOH, —(CH$_2$)$_b$NR$^{z1}$R$^{z2}$ or —(CH$_2$)$_2$POR$^{z3}$R$^{z4}$;
b is 2, 3, 4, 5 or 6;
$R^{z1}$ and $R^{z2}$ are independently hydrogen or $C_1$–$C_4$ alkyl; and
$R^{z3}$ and $R^{z4}$ are independently hydrogen or methoxy;
or a pharmaceutically acceptable salt thereof.

51. A method according to claim 50 where the compound is one where:

$R^{x1}$ is methyl, benzyl, —CH$_2$CHOHCH$_2$OH, —CH$_2$COOH, —(CH$_2$)$_2$NR$^{z1}$R$^{z2}$ or —(CH$_2$)$_2$POR$^{z3}$R$^{z4}$;

$R^{z1}$ and $R^{z2}$ are independently hydrogen or methyl; and
$R^{z3}$ and $R^{z4}$ are independently hydrogen or methoxy;
or a pharmaceutically acceptable salt thereof.

52. A method according to claim 51 where the compound is one where:
$R^{x1}$ is —CH$_2$CHOHCH$_2$OH, —CH$_2$COOH or —(CH$_2$)$_2$POR$^{z3}$R$^{z4}$; and
$R^{z3}$ and $R^{z4}$ are independently hydrogen or methoxy;
or a pharmaceutically acceptable salt thereof.

53. The method according to claim 52 where the compound is one where:
$R_0$ is hydroxy;

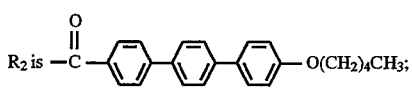

and
$R^{x1}$ is —CH$_2$CHOHCH$_2$OH;
or a pharmaceutically acceptable salt thereof.

54. A method according to claim 51 where the compound is one where:
$R_0$ is hydroxy;

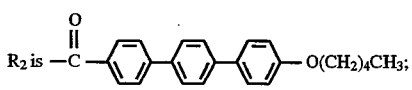

and
$R^{x1}$ is methyl;
or a pharmaceutically acceptable salt thereof.

55. A method according to claim 50 where the parasite is *Pneumcystis carinii*.

56. A method for treating or preventing the onset of Pneumocystis pneumonia in a host susceptible to Pneumocystis pneumonia which comprises administering an effective amount of a compound of formula I, or a pharmaceutically acceptable salt thereof, to a host in need of such treatment.

57. A method according to claim 56 where the compound is one where:
R', R" and R'" are each methyl;
$R^{y1}$, $R^{y2}$, $R^{y3}$ and $R^{y4}$ are each hydroxy;
$R^{x2}$ is hydroxy;
$R_0$ is hydroxy or a group of the formulae:

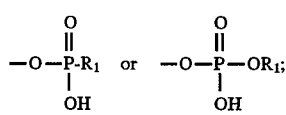

$R_1$ is methyl;
or a pharmaceutically acceptable salt thereof.

58. A method according to claim 57 where the compound is one where:

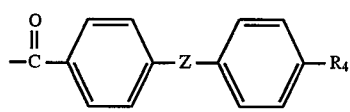

where
Z is —C≡C— or a bond;
A) R$_4$ is hydrogen, C$_1$–C$_{12}$ alkyl, C$_1$–C$_{12}$ substituted alkyl, C$_2$–C$_{12}$ alkenyl, C$_2$–C$_{12}$ substituted alkenyl, C$_2$–C$_{12}$ alkynyl, C$_2$–C$_{12}$ substituted alkynyl, C$_1$–C$_{12}$ alkoxy, C$_3$–C$_{12}$ cycloalkyl, C$_7$–C$_{10}$ bicycloalkyl, C$_7$–C$_{14}$ tricycloalkyl, C$_3$–C$_{12}$ cycloalkoxy, naphthyl, pyridyl, thienyl, benzothienyl, quinolyl or phenyl; or B) R$_4$ is phenyl substituted by amino, C$_1$–C$_{12}$ alkylthio, halo, C$_1$–C$_{12}$ alkyl, C$_2$–C$_{12}$ alkenyl, C$_2$–C$_{12}$ alkynyl, C$_1$–C$_{12}$ substituted alkyl, C$_2$–C$_{12}$ substituted alkenyl, C$_2$–C$_{12}$ substituted alkynyl, C$_1$–C$_{12}$ alkoxy, trifluoromethyl, phenyl, substituted phenyl, or a group of the formula —O—(CH$_2$)$_m$—[O—(CH$_2$)$_n$]$_p$—O—(C$_1$–C$_{12}$ alkyl) where m, n and p are as defined above; or C) R$_4$ is C$_1$–C$_{12}$ alkoxy substituted with halo, C$_3$–C$_{12}$ cycloalkyl, C$_7$–C$_{10}$ bicycloalkyl, C$_7$–C$_{14}$ tricycloalkyl, C$_1$–C$_6$ alkoxy, C$_2$–C$_{12}$ alkynyl, amino, C$_1$–C$_4$ alkylamino, di(C$_1$–C$_4$ alkyl)amino, formamido, C$_2$–C$_{12}$ alkanoylamino, or phenyl substituted with a group of the formula —O—(CH$_2$)$_m$—[O—(CH$_2$)$_n$]$_p$—O—(C$_1$–C$_{12}$ alkyl) where m, n and p are as defined above; or D) R$_4$ is —O—(CH$_2$)$_r$—W—R$_5$;
r is 2, 3 or 4;
W is pyrrolidino, piperidino or piperazino;
R$_5$ is hydrogen, C$_1$–C$_{12}$ alkyl, C$_3$–C$_{12}$ cycloalkyl, benzyl or C$_3$–C$_{12}$ cycloalkylmethyl; or E) R$_4$ is —Y$^1$—R$_6$;
Y$^1$ is —C≡C— or —CH=CH—;
R$_6$ is C$_3$–C$_{12}$ cycloalkyl, C$_7$–C$_{10}$ bicycloalkyl, C$_7$–C$_{14}$ tricycloalkyl, C$_3$–C$_{12}$ cycloalkenyl, naphthyl, benzothiazolyl, thienyl, indanyl, fluorenyl, or phenyl substituted with C$_1$–C$_{12}$ alkylthio, C$_2$–C$_{12}$ alkenyl, C$_2$–C$_{12}$ alkynyl, halo(C$_1$–C$_6$ alkoxy) or a group of the formula —O—(CH$_2$)$_r$—W—R$_5$ where r, W and R$_5$ are as defined above; or
R$_6$ is phenyl substituted with a group of the formula —O—(CH$_2$)$_m$—[O—(CH$_2$)$_n$]$_p$—O—(C$_1$–C$_{12}$ alkyl) where m, n and p are as defined above; or F) R$_4$ is C$_1$–C$_{12}$ alkoxy substituted with a group of the formula —NHC(O)R$_7$;
R$_7$ is C$_1$–C$_6$ alkoxy, or phenyl(C$_1$–C$_6$ alkoxy);
or a pharmaceutically acceptable salt thereof.

59. A method according to claim 58 where the compound is one where:
A) R$_4$ is C$_2$–C$_{12}$ alkynyl, C$_2$–C$_{12}$ substituted alkynyl, C$_1$–C$_{12}$ alkoxy, C$_3$–C$_{12}$ cycloalkoxy, or phenyl; or
B) R$_4$ is phenyl substituted by C$_1$–C$_{12}$ alkoxy, or a group of the formula —O—(CH$_2$)$_2$—O—(C$_1$–C$_6$ alkyl); or
C) R$_4$ is C$_1$–C$_{12}$ alkoxy substituted with C$_3$–C$_{12}$ cycloalkyl; or
D) R$_4$ is —O—(CH$_2$)$_r$—W—R$_5$;
r is 2 or 3;
W is piperidino;
R$_5$ is hydrogen, C$_1$–C$_{12}$ alkyl, C$_3$–C$_{12}$ cycloalkyl, benzyl or C$_3$–C$_{12}$ cycloalkylmethyl; or
E) R$_4$ is —Y$^1$—R$_6$;
Y$^1$ is —C≡C—;
R$_6$ is phenyl substituted with C$_1$–C$_{12}$ alkylthio, C$_2$–C$_{12}$ alkenyl, C$_2$–C$_{12}$ alkynyl, halo(C$_1$–C$_6$ alkoxy);
or R$_6$ is phenyl substituted with a group of the formula —O—(CH$_2$)$_r$—W—R$_5$ where r, W and R$_5$ are as defined above;
or R$_6$ is phenyl substituted with a group of the formula —O—(CH$_2$)$_2$—O—(C$_1$–C$_6$ alkyl);
or a pharmaceutically acceptable salt thereof.

60. A method according to claim 59 where the compound is one where:

$R_4$ is $C_2$-$C_{12}$ alkynyl, $C_2$-$C_{12}$ substituted alkynyl, $C_1$-$C_{12}$ alkoxy, or phenyl; or $R_4$ is phenyl substituted by $C_1$-$C_{12}$ alkoxy, or a group of the formula —O—$(CH_2)_2$—O—$(C_1$-$C_6$ alkyl); or $R_4$ is —$Y^1$—$R_6$;

$Y^1$ is —C≡C—;

$R_6$ is phenyl substituted with a group of the formula —O—$(CH_2)_2$—O—$(C_1$-$C_6$ alkyl);

or a pharmaceutically acceptable salt thereof.

61. A method according to claim 60 where the compound is one where:

$R^{x1}$ is $C_1$-$C_4$ alkyl, benzyl, —$CH_2CHOHCH_2OH$, —$CH_2COOH$, —$(CH_2)_b NR^{z1} R^{z2}$ or —$(CH_2)_2 POR^{z3}R^{z4}$;

b is 2, 3, 4, 5 or 6;

$R^{z1}$ and $R^{z2}$ are independently hydrogen or $C_1$-$C_4$ alkyl; and $R^{z3}$ and $R^{z4}$ are independently hydrogen or methoxy;

or a pharmaceutically acceptable salt thereof.

62. A method according to claim 61 where the compound is one where:

$R^{x1}$ is methyl, benzyl, —$CH_2CHOHCH_2OH$, —$CH_2COOH$, —$(CH_2)_2 NR^{z1} R^{z2}$ or —$(CH_2)_2 POR^{z3}R^{z4}$;

$R^{z1}$ and $R^{z2}$ are independently hydrogen or methyl; and $R^{z3}$ and $R^{z4}$ are independently hydrogen or methoxy;

or a pharmaceutically acceptable salt thereof.

63. A method according to claim 62 where the compound is one where:

$R^{x1}$ is —$CH_2CHOHCH_2OH$, —$CH_2COOH$ or —$(CH_2)_2 POR^{z3}R^{z4}$; and $R^{z3}$ and $R^{z4}$ are independently hydrogen or methoxy;

or a pharmaceutically acceptable salt thereof.

64. The method according to claim 63 where the compound is one where:

$R_0$ is hydroxy;

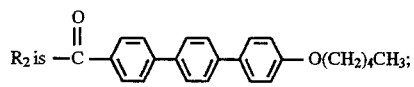

and $R^{x1}$ is —$CH_2CHOHCH_2OH$;

or a pharmaceutically acceptable salt thereof.

65. The method according to claim 62 where the compound is one where:

$R_0$ is hydroxy;

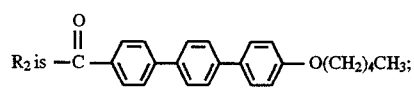

and $R^{x1}$ is methyl;

or a pharmaceutically acceptable salt thereof.

* * * * *